(12) United States Patent
Bajaj

(10) Patent No.: US 8,993,719 B2
(45) Date of Patent: Mar. 31, 2015

(54) METHODS AND COMPOSITIONS RELATED TO MUTANT KUNITZ DOMAIN I OF TFPI-2

(75) Inventor: S. Paul Bajaj, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1344 days.

(21) Appl. No.: 12/087,296

(22) PCT Filed: Dec. 29, 2006

(86) PCT No.: PCT/US2006/062723
§ 371 (c)(1),
(2), (4) Date: Jun. 30, 2008

(87) PCT Pub. No.: WO2007/076537
PCT Pub. Date: Jul. 5, 2007

(65) Prior Publication Data
US 2009/0018069 A1 Jan. 15, 2009

Related U.S. Application Data

(60) Provisional application No. 60/754,731, filed on Dec. 29, 2005.

(51) Int. Cl.
*A61K 38/16* (2006.01)
*C07K 14/00* (2006.01)
*A61K 38/00* (2006.01)
*C07K 14/81* (2006.01)
*A61K 48/00* (2006.01)

(52) U.S. Cl.
CPC ......... *C07K 14/8114* (2013.01); *A01K 2217/05* (2013.01); *A01K 2227/105* (2013.01); *A01K 2267/0375* (2013.01); *A61K 48/00* (2013.01)
USPC ........................................ 530/324; 514/21.3

(58) Field of Classification Search
None
See application file for complete search history.

(56) References Cited

U.S. PATENT DOCUMENTS

| | | | |
|---|---|---|---|
| 4,595,674 A | 6/1986 | Tschesche et al. | |
| 4,894,436 A | 1/1990 | Auerswald et al. | |
| 5,032,573 A | 7/1991 | Auerswald et al. | |
| 5,455,338 A | 10/1995 | Sprecher et al. | |
| 5,663,143 A | 9/1997 | Ley | 514/12 |
| 5,728,674 A | 3/1998 | Sprecher et al. | |
| 5,795,865 A | 8/1998 | Markland et al. | |
| 5,914,315 A | 6/1999 | Sprecher et al. | |
| 5,981,471 A | 11/1999 | Papathanassiu et al. | |
| 6,010,880 A | 1/2000 | Markland et al. | |
| 6,057,287 A | 5/2000 | Markland et al. | |
| 6,071,723 A | 6/2000 | Markland et al. | |
| 6,103,499 A * | 8/2000 | Markland et al. | 435/69.2 |
| 6,333,402 B1 | 12/2001 | Markland | 526/23.5 |
| 6,423,498 B1 | 7/2002 | Markland et al. | |
| 6,656,746 B2 | 12/2003 | Sprecher et al. | |
| 6,953,674 B2 | 10/2005 | Markland | 435/6 |
| 7,070,969 B1 | 7/2006 | Masci | |
| 7,078,383 B2 | 7/2006 | Ley et al. | |
| 7,432,238 B2 | 10/2008 | Kisiel et al. | |
| 7,585,842 B2 * | 9/2009 | Kisiel et al. | 514/1.1 |
| 7,628,983 B2 | 12/2009 | Markland et al. | |
| 7,919,462 B2 | 4/2011 | Markland et al. | |
| 8,283,321 B2 | 10/2012 | Markland et al. | |
| 2004/0229312 A1* | 11/2004 | Bougueleret et al. | 435/69.1 |
| 2004/0253686 A1 | 12/2004 | Sprecher et al. | |
| 2005/0004021 A1 | 1/2005 | Sprecher et al. | |
| 2005/0186649 A1 | 8/2005 | Markland et al. | |
| 2005/0222023 A1 | 10/2005 | Hauser et al. | |
| 2009/0018069 A1 | 1/2009 | Bajaj | |
| 2011/0152193 A1 | 6/2011 | Markland et al. | |

FOREIGN PATENT DOCUMENTS

| | | | | |
|---|---|---|---|---|
| CN | 1634986 | * | 7/2005 | ............. A61K 38/17 |
| WO | WO 93/14120 | | 7/1993 | |
| WO | 95/18830 A2 | | 7/1995 | |
| WO | WO 95/18830 | | 7/1995 | |

OTHER PUBLICATIONS

Chand et al. (Structure-funtions analysis of the reactive site in the first Kunitz-type domain of human tissue factor pathway inhibitor-2. The Journal of Biological Chemistry. Apr. 23, 2004, vol. 279, No. 17, pp. 17500-17507).*
Schmidt et al. (Crystal Struture of Kunitz domain 1 (KDI) of tissue factor pathway inhibitor-2 in comples with trypsin. The Journal of Chemistry. Jul. 29, 2005, vol. 280, No. 30, 27832-27838.*
Communication pursuant to Article 94(3) EPC issued Jul. 19, 2011 for European Patent Application No. 06848474.0, which claims priority to PCT/US2006/062723 filed Dec. 29, 2006 (Inventor: S.P. Bajaj; Applicant: Regents of the University of California) (3 pages).
Response to Article 94(3) EPC Communication filed Jul. 4, 2011 for European Patent Application No. 06848474.0, which claims priority to PCT/US2006/062723 filed Dec. 29, 2006 (Inventor: S.P. Bajaj; Applicant: Regents of the University of California) (13 pages).
U.S. Appl. No. 60/754,913, filed Dec. 29, 2005, Kisiel et al.
U.S. Appl. No. 60/754,731, filed Dec. 29, 2005, Bajaj.
Abdulkadir et al. (2000) Tissue factor expression and angiogenesis in human prostate carcinoma. Hum Pathol. 31(4): 443-447.
AC 035536, Tissue Factor Pathway Inhibitor 2 precursor (TFPI-2) from mouse, 230 amino acids.
Andre et al. (2000) Vegf, Vegf-B, Vegf-C and their receptors KDR, FLT-1 and FLT-4 during the neoplastic progression of human colonic mucosa.f Int. J. Cancer.86(2): 174-181.
Bajaj et al. (2001) Structure and biology of tissue factor pathway inhibitor. Thromb Haemost. 86(4): 959-972.
Bajaj, Molecular Recognition in Factor VIIa Induced Coagulation, Grant Abstract, Grant No. 1R01HL070369-01. National Institute of Health, Apr. 1, 2002 to Mar. 31, 2006.
Bajaj, Molecular Recognition in Factor VIIa Induced Coagulation, Grant Abstract, Grant No. 5R01HL070369-02. National Institute of Health, Apr. 1, 2002 to Oct. 31, 2003.
Bajaj, Molecular Recognition in Factor VIIa Induced Coagulation, Grant Abstract, Grant No. 7R01HL070369-03. National Institute of Health, Apr. 1, 2002 to Mar. 31, 2006.

(Continued)

*Primary Examiner* — Maury Audet
(74) *Attorney, Agent, or Firm* — Seed IP Law Group PLLC

(57) ABSTRACT

Disclosed are methods and compositions relating to plasmin inhibition.

29 Claims, 4 Drawing Sheets

(56) References Cited

OTHER PUBLICATIONS

Bajaj, Molecular Recognition in Factor VIIa Induced Coagulation, Grant Abstract, Grant No. 5R01HL070369-04. National Institute of Health, Apr. 1, 2002 to Mar. 31, 2006.
Bajaj, Molecular Recognition in Factor VIIa Induced Coagulation, Grant Abstract, Grant No. 5R01HL070369-05. National Institute of Health, Apr. 1, 2002 to Mar. 31, 2007.
Banner et al. (1996) The crystal structure of the complex of blood coagulation factor VIIa with soluble tissue factor. Nature. 380(6569): 41-46.
Beierlein et al. (2005) Forty years of clinical aprotinin use: a review of 124 hypersensitivity reactions. Ann Thorac Surg. 79(2): 741-748.
Bernstein et al. (2002) Comparison of techniques for the successful detection of BRCA1 mutations in fixed paraffin-embedded tissue. Cancer Epid. Biomark. Prey. 11(9): 809-814.
Bieth JG. (1984) In vivo significance of kinetic constants of protein proteinase inhibitors. Biochem. Med. 32(3): 387-397.
Bizik et al. (1990) Plasminogen activation by t-PA on the surface of human melanoma cells in the presence of alpha 2-macroglobulin secretion. Cell Regul. 1(12): 895-905.
Bode et al. (2000) Structural basis of the endoproteinase-protein inhibitor interaction. Biochim. Biophys. Acta. 1477(1-2): 241-252.
Bodner et al. (2003) CD4 dependence of gp120IIIB-CXCR4 interaction is cell-type specific. J. Neuroimmunol. 140(1-2): 1-12.
Bowie et al., Deciphering the message in the protein sequences: Tolerance to amino acid substitutions (1990) Science, vol. 247, pp. 1306-1310.
Bradford MM. (1976) A rapid and sensitive method for the quantitation of microgram quantities of protein utilizing the principle of protein-dye binding. Anal. Biochem. 72: 248-254.
Broze et al. (1990) Regulation of coagulation by a multivalent Kunitz-type inhibitor. Biochemistry. 29(33): 7539-7546.
Burgering et al. (1997) The second Kunitz domain of human tissue factor pathway inhibitor: cloning, structure determination and interaction with factor Xa. J. Mol. Biol. 269(3): 395-407.
Castellino et al. (2005) Structure and function of the plasminogen/plasmin system. Thromb Haemost. 93(4): 647-654.
Castro et al. (1996) Alanine point-mutations in the reactive region of bovine pancreatic trypsin inhibitor: effects on the kinetics and thermodynamics of binding to beta-trypsin and alpha-chymotrypsin. Biochemistry. 35(35): 11435-11446.
Chand et al. (2004) Structure-function analysis of the reactive site in the first Kunitz-type domain of human tissue factor pathway inhibitor-2. J Biol Chem. 279(17): 17500-17507.
Chand et al. (2004) The effect of human tissue factor pathway inhibitor-2 on the growth and metastasis of fibrosarcoma tumors in athymic mice. Blood. 103(3): 1069-1077.
Chau et al. (2000) Aven, a novel inhibitor of caspase activation, binds Bcl-xL and Apaf-1. Mol. Cell. 6(1): 31-40.
Choong et al. (2003) Urokinase plasminogen activator system: a multifunctional role in tumor progression and metastasis. Clin Orthop Relat Res. 415 Suppl: S46-S58.
Cohen et al. (1972) Nonchromosomal antibiotic resistance in bacteria: genetic transformation of *Escherichia coli* by R-factor DNA. Proc. Natl. Acad. Sci. USA. 69(8): 2110-2114.
Coligan et al. Production of Polyclonal Antisera in Rabbits, Rats, Mice and Hamsters, Section 2.4.1 and 2.5.1-2.6.7, Current Protocols in Immunology, Hoboken, NJ.
Coligan et al. Unit 9, Current Protocols in Immunology, Wiley Interscience, Hoboken, NJ.
Cottrell et al. (2004) Trypsin IV, a novel agonist of protease-activated receptors 2 and 4. J. Biol. Chem. 279(14): 13532-13539.
Crawley et al. (2002) Expression and localization of tissue factor pathway inhibitor-2 in normal and artherosclerotic human vessels. Artherioscler. Thromb. Vasc. Biol. 22(2): 218-224.
Creighton et al. (1987) Sequences of the genes and polypeptide precursors for two bovine protease inhibitors. J. Mol. Biol. 194(1): 11-22.
Crowley et al. (1993) Prevention of Metastasis by Inhibition of the Urokinase Receptor. Proc. Natl. Acad. Sci. USA. 90(11): 5021-5025.
Daci et al. (1999) The role of the plasminogen system in bone resorption in vitro. J Bone Miner Res. 14(6): 946-952.
Daci et al. (2003) Increased bone formation in mice lacking plasminogen activators. J Bone Miner Res. 18(7): 1167-1176.
Dano et al. (1985) Plasminogen activators, tissue degradation, and cancer. Adv. Cancer Res. 44: 139-266.
Day et al. (2004) Clinical inhibition of the seven-transmembrane thrombin receptor (PAR1) by intravenous aprotinin during cardiothoracic surgery. Circulation. 110(17): 2597-2600.
Deng et al. (2001) Urothelial function reconsidered: a role in urinary protein secretion. Proc. Natl. Acad. Sci USA. 98(1): 154-159.
Drobnic-Kosorok et al. (1990) A new inhibitor of plasmin and trypsin from porcine leukocytes. Biol. Chem. Hoppe Seyler. 371(1): 57-61.
Du et al. (2003) Human tissue factor pathway inhibitor-2 does not bind or inhibit activated matrix metalloproteinase-1. Biochim Biophys Acta. 1621(3): 242-245.
Du et al. (2003) Molecular cloning, expression, and characterization of bovine tissue factor pathway inhibitor-2. Arch Biochem Biophys. 417(1): 96-104.
Ekstrand et al. (2003) Deletion of neuropeptide Y (NPY) 2 receptor in mice results in blockage of NPY-induced angiogenesis and delayed wound healing. Proc. Natl. Acad. Sci USA. 100(10): 6033-6038.
Flight et al. (2005) Comparison of textilinin-1 with aprotinin as serine protease inhibitors and as antifibrinolytic agents. Pathophysiol Haemost Thromb. 34(4-5): 188-193.
Gans et al. (1967) Problems in hemostasis during open heart surgery. IX. Changes observed in the plasminogen-plasmin system and their significance for therapy. Ann Surg. 166(6): 980-986.
Gerber et al. (2000) Complete inhibition of rhabdomyosarcoma xenograft growth and neovascularization requires blockade of both tumor and host vascular endothelial growth factor. Cancer Res. 60(22): 6253-6258.
Gill et al. (1989) Calculation of protein extinction coefficients from amino acid sequence data. Anal. Biochem. 182(2): 319-326.
Girard et al. (1989) Functional significance of the Kunitz-type inhibitory domains of lipoprotein-associated coagulation inhibitor. Nature. 338(6215): 518-520.
Gram et al. (1992) In vitro selection and affinity maturation of antibodies from a naive combinatorial immunoglobulin library. Proc. Natl. Acad. Sci. USA. 89(8): 3576-3580.
Green et al. (1992) Production of Polyclonal Antisera; Immunochemical Protocols, Chapter 1. Manson (ed.) Humana Press; Totowa, NJ.
Grzesiak et al. (2000) Inhibition of six serine proteinases of the human coagulation system by mutants of bovine pancreatic trypsin inhibitor. J. Biol. Chem. 275(43): 33346-33352.
Harlow et al. (1988) Antibodies A Laboratory Manual, Cold Spring Harbor Laboratory. Cold Spring Harbor, NY.
Herman et al. (2001) Tissue factor pathway inhibitor-2 is a novel inhibitor of matrix metalloproteinases with implications for atherosclerosis. J. Clin. Invest. 107(9):1117-1126.
Hilal et al. (1998) Osteoblast-like cells from human subchondral osteoarthritic bone demonstrate and altered phenotype in vitro: possible role in subchondral bone sclerosis. Arthritis Rheum. 41(5): 891-899.
Hisaka et al. (2004) Expression of tissue factor pathway inhibitor-2 in murine and human liver regulation during inflammation. Thromb Haemost. 91(3): 569-575.
Huber et al. (1974) Structure of the complex formed by bovine trypsin and bovine pancreatic trypsin inhibitor. II. Crystallographic refinement at 1.9 A resolution. J Mol Biol. 89(1): 73-101.
Iino et al. (1998) Quantification and characterization of human endothelial cell-derived tissue factor pathway inhibitor-2. Arterioscler Thromb Vasc Biol. 18(1): 40-46.
Izumi et al. (2000) Tissue factor pathway inhibitor-2 suppresses the production of active matrix metalloproteinase-2 and is down-regulated in cells harboring activated ras oncogenes. FEBS Lett. 481(1): 31-36.
Janin et al. (1990) The structure of protein-protein recognition sites. J. Biol. Chem. 265(27): 16027-16030.

(56) References Cited

OTHER PUBLICATIONS

Jin et al. (2001) Expression of serine proteinase inhibitor PP5/TFPI-2/MSPI decreases the invasive potential of human choriocarcinoma cells in vitro and in vivo. Gyn. Oncol. 83(2): 325-333.

Judex et al. (2005) Plasminogen activation/plasmin in rheumatoid arthritis: matrix degradation and more. Am J Pathol. 166(3): 645-647.

Kamei et al. (1999) Inhibitory properties of human recombinant $Arg^{24} \rightarrow Gln$ type-2 tissue factor pathway inhibitor (R24Q TFPI-2). Thromb. Res. 94(3): 147-152.

Kamei et al. (2001) Genomic structure and promoter activity of the human tissue factor pathway inhibitor-2 gene. Biochim Biophys Acta. 1517(3): 430-435.

Kaumeyer et al. (1986) The mRNA for a proteinase inhibitor related to the HI-30 domain of inter-alpha-trypsin inhibitor also encodes alpha-1-microgulobulin (Protein HC). Nucleic Acids Res. 14(20): 7839-7850.

Kawaguchi et al. (1997) Purification and cloning of hepatocyte growth factor activator inhibitor type 2, a Kunitz-type serine protease inhibitor. J. Biol. Chem. 272(44): 27558-27564.

Kay et al. (ed.) Phage display of peptides and protiens: A laboratory manual. Academic Press, San Diego, CA (1996).

Kazama et al. (2000) Nucleotide sequence of the gene encoding murine tissue factor pathway inhibitor-2. Thromb Haemost. 83(1): 141-147.

Kermani et al. (1995) Production of ScFv antibody fragments following immunization with a phage-displayed fusion protein and analysis of reactivity to surface-exposed epitopes of the protein F of *Pseudomonas aeruginosa* by cytofluorometry. Hybridoma. 14(4): 323-328.

Kisiel et al. (1985) Proteolytic inactivation of blood coagulation factor IX by thrombin. Blood. 66(6): 1302-1308.

Kisiel, Type-2 Tissue Factor Pathway Inhibitor, Grant Abstract, Grant No. 1R01HL064119-01A1. National Institute of Health, Sep. 5, 2000 to Jul. 31, 2004.

Kisiel, Type-2 Tissue Factor Pathway Inhibitor, Grant Abstract, Grant No. 5R01HL064119-02. National Institute of Health, Sep. 5, 2000 to Jul. 31, 2004.

Kisiel, Type-2 Tissue Factor Pathway Inhibitor, Grant Abstract, Grant No. 5R01HL064119-03. National Institute of Health, Sep. 5, 2000 to Jul. 31, 2004.

Kisiel, Type-2 Tissue Factor Pathway Inhibitor, Grant Abstract, Grant No. 5R01HL064119-04. National Institute of Health, Sep. 5, 2000 to Jul. 31, 2004.

Kisiel, Type-2 Tissue Factor Pathway Inhibitor, Grant Abstract, Grant No. 2R01HL064119-05. National Institute of Health, Dec. 1, 1999 to Jul. 31, 2009.

Kisiel, Type-2 Tissue Factor Pathway Inhibitor, Grant Abstract, Grant No. 5R01HL064119-06. National Institute of Health, Dec. 1, 1999 to Jul. 31, 2009.

Kisiel, Type-2 Tissue Factor Pathway Inhibitor, Grant Abstract, Grant No. 5R01HL064119-07. National Institute of Health, Dec. 1, 1999 to Jul. 31, 2009.

Kobayashi et al. (2004) Therapeutic efficacy of once-daily oral administration of a Kunitz-type protease inhibitor, bikunin, in a mouse model and in human cancer. Cancer. 100(4):869-877.

Köhler et al. (1975) Continuous cultures of fused cells secreting antibody of predefined specificity. Nature. 256(5517): 495-497.

Kokoszka et al. (2005) Evidence-based review of the role of aprotinin in blood conservation during orthopaedic surgery. J Bone Joint Surg Am. 87(5): 1129-1136.

Konduri et al. (2001) A novel function of tissue factor pathway inhibitor-2 (TFPI-2) in human glioma invasion. Oncogene. 20(47): 6938-6945.

Konduri et al. (2002) Minimal and inducible regulation of tissue factor pathway inhibitor-2 in human gliomas. Oncogene. 21(6): 921-928.

Konduri et al. (2003) Physiological and chemical inducers of tissue factor pathway inhibitor-2 in human glioma cells. Int J Oncol. 22(6): 1277-1283.

Konduri et al. (2003) Promoter methylation and silencing of the tissue factor pathway inhibitor-2 (TFPI-2), in human glioma cells. Oncogene. 22(29): 4509-4516.

Kramer et al. (1994) Plasmin in pericellular proteolysis and cellular invasion. Invasion Metastasis. 14: 210-222.

Kraunsoe et al. (1996) An investigation of the binding of protein proteinase inhibitors to trypsin by electrospray ionization mass spectrometry. FEBS Lett. 396(1): 108-112.

Kwaan et al. (1992) The plasminogen-plasmin system in malignancy. Cancer Metastasis Rev. 11(3-4): 291-311.

Laemmli UK. (1970) Cleavage of structural proteins during the assembly of the head of bacteriophage T4. Nature. 227(5259): 680-685.

Lane et al. (1986) High Efficiency Fusion Procedure for Producing Monoclonal Antibodies against Weak Immunogens. Methods in Enzymology. 121: 183-192.

Laskowski et al. (1980) Protein inhibitors of proteinases. Ann. Rev. Biochem. 49: 593-626.

Lee et al. (2002) MIM, a potential metastasis suppressor gene in bladder cancer. Neoplasia. 4(4): 291-294.

Levy et al. (2004) Aprotinin: A Pharmacologic Overview. Orthopedics. 27(6): s653-s658.

Levy JH. (2004) Efficacy and Safety of Aprotinin in Cardiac Surgery. Orthopedics. 27(6): s659-s662.

Li et al. (2005) The plasminogen activator/plasmin system is essential for development of the joint inflammatory phase of collagen type II-induced arthritis. Am J Pathol. 166(3): 783-92.

Lijnen HR. (2005) Pleiotropic functions of plasminogen activator inhibitor-1. J Thromb Haemost. 3(1): 35-45.

Mandriota et al. (2001) Vascular endothelial growth factor-C-mediated lymphangiogenesis promotes tumour metastasis. EMBO J. 20(4): 672-682.

Mangano et al. (2006) The risk associated with aprotinin in cardiac surgery. N Engl J Med. 354(4): 353-365.

Mareel et al. (2003) Clinical, cellular, and molecular aspects of cancer invasion, Physiol. Rev. 83(2): 337-376.

Mayer et al. (eds.) Immunochemical Methods in Cell and Molecular Biology. Academic Press, London, 1987.

Mazzucchelli. (2002) Protein S100A4: too long overlooked by pathologists? Am. J. Pathol. 160(1): 7-13.

Mignatti et al. (1993) Biology and biochemistry of proteinases in tumor invasion. Physiol. Rev. 73(1): 161-195.

Minagawa et al. (2008) Kunitz-type protease inhibitors from acrorhagi of three species of sea anemones. Comp Biochem Physiol B Biochem Mol Biol. 150(2): 240-245.

Minagawa et al. (1997) Isolation and amino acid sequences of two Kunitz-type protease inhibitors from the sea anemone *Anthopleura aff. xanthogrammica*. Comp Biochem Physiol B Biochem Mol Biol. 118(2): 381-386.

Min et al. (1996) Urokinase receptor antagonists inhibit angiogenesis and primary tumor growth in syngeneic mice. Cancer Res. 56(10): 2428-2433.

Miyagi et al. (1994) cDNA cloning and mRNA expression of a serine proteinase inhibitor secreted by cancer cells: identification as placental protein 5 and tissue factor pathway inhibitor-2. J Biochem. 116(5): 939-942.

Monoclonal Antibody Production; Committee on Methods of Producing Monoclonal Antibodies. Institute for Laboratory Animal Research, National Research Council; The National Academies Press; Washington, DC, 1999.

National Center for Biotechnology Information, National Library of Medicine, National Institutes of Health, GenBank Locus AAH05330, Accession No. AAH05330, Tissue Factor Pathway Inhibitor 2 [*Homo sapiens*].

Nawrocki-Raby et al. (2003) Upregulation of MMPs by soluble E-cadherin inhuman lung tumor cells. Int. J. Cancer. 105(6): 790-795.

Neaud et al. (2004) Thrombin up-regulates tissue factor pathway inhibitor-2 synthesis through a cyclooxygenase-2-dependent, epidermal growth factor receptor-independent mechanism. J Biol Chem. 279(7): 5200-5206.

(56) References Cited

OTHER PUBLICATIONS

Neaud et al. (2000) Paradoxical pro-invasive effect of the serine proteinase inhibitor tissue factor pathway inhibitor-2 on human hepatocellular carcinoma cells. J Biol Chem. 275(45): 35565-35569.
Nicholls et al. (1991) Protein folding and association: insights from the interfacial and thermodynamic properties of hydrocarbons. Proteins. 11(4): 281-296.
Niimi. (2004) Aprotinin dosing: how much is enough? J. Extra Corpor Technol. 36(4): 384-390.
Nirmala et al. (2001) Insect silk contains both a Kunitz-type and a unique Kazal-type proteinase inhibitor. Eur. J. Biochem. 268(7): 2064-2073.
Noda et al. (2003) RECK: a novel suppressor of malignancy linking oncogenic signaling to extracellular matrix remodeling. Cancer Metastasis Rev. 22(2-3): 167-175.
Novak et al. (1997) Plasmin-mediated proteolysis of osteocalcin. J Bone Miner Res. 12(7): 1035-1042.
Oh et al. (2001) The Membrane-Anchored MMP Inhibitor RECK is a Key Regulator of Extracellular Matrix Integrity and Angiogenesis. Cell. 107: 789-800.
Olofsson et al. (1998) Vascular endothelial growth factor B (VEGF-B) binds to VEGF receptor-1 and regulates plasminogen activator activity in endothelial cells. Proc. Natl. Acad. Sci. USA. 95(20): 11709-11714.
Osawa et al. (2002) Tumor necrosis factor alph-induced interleukin-8 production via NF-kappaB and phosphatidylinositol 3-kinase/Akt pathways inhibits cell apoptosis in human hepatocytes. Infect. Immun. 70(11): 6294-6301.
Perona et al. (1997) Evolutionary Divergence of Substrate Specificity within the Chymotrypsin-like Serine Protease Fold. J. Biol. Chem. 272(48): 29987-29990.
Petersen et al. (1996) Inhibitory properties of a novel human Kunitz-type protease inhibitor homologous to tissue factor pathway inhibitor. Biochemistry. 35(1): 266-272.
Physician's Desk Reference. (2004) Aprotinin dosing regimen. p. 864.
Ponte et al. (1988) A new A4 amyloid mRNA contains a domain homologous to serine proteinase inhibitors. Nature. 331: 525-527.
Potempa et al. (1994) The Serpin Superfamily of Proteinase Inhibitors: Structure, Function, and Regulation. J. Biol. Chem. 269(23): 15957-15960.
Quax et al. (1991) Metastatic behavior of human melanoma cell lines in nude mice correlates with urokinase-type plasminogen activator, its type-1 inhibitor, and urokinase-mediated matrix degradation. J. Cell Biol. 115(1): 191-199.
Rao et al. (1995) Novel extracellular matrix-associated serine proteinase inhibitors from human skin fibroblasts. Arch. Biochem. Biophys. 317(1): 311-314.
Rao et al. (1995) Partial characterization of matrix-associated serine protease inhibitors from human skin cells. J Invest Dermatol. 104(3): 379-383.
Rao et al. (1996) Extracellular matrix-associated serine protease inhibitors (Mr 33,000, 31,000, and 27,000) are single-gene products with differential glycosylation: cDNA cloning of the 33-kDa inhibitor reveals its identity to tissue factor pathway inhibitor-2. Arch Biochem Biophys. 335(1): 82-92.
Rao et al. (1997) HT-1080 fibrosarcoma cell matrix degradation and invasion are inhibited by the matrix-assiciated serine protease inhibitor TFPI-2/33 kDA MSPI. Int. J. Cancer. 76(5): 749-756.
Rao et al. (1999) Regulation of ProMMP-1 and ProMMP-3 activation by tissue factor pathway inhibitor-2/matrix-associated serine protease inhibitor. Biochem. Biophys. Res. Commun. 255(1): 94-98. Erratum in Biochem. Biophys. Res. Commun. (1999) 258(2): 497.
Regents of the University of New Mexico, Grant Contracts Press Release, Grant No. N00178-01-C-3069. United States Department of Defense, 2001.
Reinartz et al. (1993) Binding and activation of plasminogen at the surface of human keratinocytes. Exp. Cell Res. 208(1): 197-208.
Rodriguez-Manzaneque et al. (2001) Thrombospondin-1 suppresses spontaneous tumor growth and inhibits activation of matrix metalloproteinase-9 and mobilization of vascular endothelial growth factor. Proc. Natl. Acad. Sci. USA. 98(22): 12485-12490.
Ronday et al. (1997) Bone matrix degradation by the plasminogen activation system. Possible mechanism of bone destruction in arthritis. Br J Rheumatol. 36(1): 9-15.
Roy et al. (2002) Matrix Gla protein binding to hydroxyapatite is dependent on the ionic environment: calcium enhances binding affinity but phosphate and magnesium decrease affinity. Bone. 31(2): 296-302.
Rudinger, Peptide Hormones, University Park Press, 1976, Baltimore, MD., pp. 1-7.
Ryniers et al. (2002) Plasmin produces an E-cadherin fragment that stimulates cancer cell invasion. Biol. Chem. 383(1): 159-165.
Sakamaki et al. (2001) Activities of plasminogen activator, plasmin and kallikrein in synovial fluid from patients with temporomandibular joint disorders. Int J Oral Maxillofac Surg. 30(4): 323-328.
Sambrook et al. (2001) Molecular Cloning: A Laboratory Manual, Third Edition, Cold Spring Harbor Laboratory Press, Cold Spring Harbor, NY, 2001. Cover page, copyright page and table of contents, 22 pages.
Sanna et al. (1995) Directed selection of recombinant human monoclonal antibodies to herpes simplex virus glycoproteins from phage display libraries. Proc. Natl. Acad. Sci. USA. 92(14): 6439-6443.
Sawaji et al. (2002) Anti-angiogenic action of hyperthermia by suppressing gene expression and production of tumour-derived vascular endothelial growth factor in vivo and in vitro. Br. J. Cancer. 86(10): 1597-1603.
Scheidig et al. (1997) Crystal structures of bovine chymotrypsin and trypsin complexed to the inhibitor domain of Alzheimer's amyloid-beta-protein precursor (APPI) and basic pancreatic trypsin inhibitor (BPTI): engineering of inhibitors with alteredspecificities. Protein Sci. 6(9): 1806-1824.
Schmidt et al. (2004) Crystal Structure of Kunitz Domain 1 (KD1) of Tissue Factor Pathway Inhibitor-2 with Trypsin and Molecular Model of K1 with Plasmin and VIIa/Tissue Factor: Implications for KD1 Specificity of Inhibition. Blood. 104(11): 38a.
Schmidt et al. (2005) Crystal structure of Kunitz domain 1 (KD1) of tissue factor pathway inhibitor-2 in complex with trypsin. Implications for KD1 specificity of inhibition. J Biol Chem. 280(30): 27832-27838.
Schmitz et al. (2000) Phage display: a molecular tool for the generation of antibodies—a review. Placenta. 21(Suppl. A): S106-S112.
Schweitz et al. (1995) Kalicludines and Kaliseptine: Two Different Classes of Sea Anemone Toxins for Voltage-Sensitive K$^+$ Channels. J. Biol. Chem. 270(42): 25121-25126.
Shahian et al. (1990) Open-heart surgery in a patient with heterozygous alpha 2-antiplasmin deficiency. Perioperative strategies in the first reported case. Chest. 97(6): 1488-1490.
Shapiro et al. (1989) Site-directed mutagenesis of histidine-13 and histidine-114 of human angiogenin. Alanine derivatives inhibit angiogenin-induced angiogenesis. Biochemistry. 28(18): 7401-7408.
Shih et al. (2002) Molecular profiling of angiogenesis markers. Am J Pathol. 161(1): 35-41.
Shimomura et al. (1997) Hepatocyte Growth Factor Activator Inhibitor, a Novel Kunitz-type Serine Protease Inhibitor. J. Biol. Chem. 272(10): 6370-6376.
Soff et al. (1995) Expression of plasminogen activator inhibitor type 1 by human prostate carcinoma cells inhibits primary tumor growth, tumor-associated angiogenesis, and metastasis to lung and liver in an athymic mouse model. J. Clin. Invest. 96(6): 2593-2600.
Sprecher et al. (1994) Molecular cloning, expression, and partial characterization of a second human tissue-factor-pathway inhibitor. Proc Natl Acad Sci USA. 91(8): 3353-3357.
Stahl et al. (1994) Binding of urokinase to its receptor promotes migration and invasion of human melanoma cells in vitro. Cancer Res. 54(11): 3066-3071.
Stallings-Mann et al. (1994) Purification, characterization, and cDNA cloning of a Kunitz-type proteinase inhibitor secreted by the porcine uterus. J. Biol. Chem. 269(39): 24090-24094.

(56) References Cited

OTHER PUBLICATIONS

Stassen et al (1995) Characterisation of a novel series of aprotinin-derived anticoagulants. II. Comparative antithrombotic effects on primary thrombus formation in vivo. Thromb. Haemost. 74(2): 655-659.
Stone et al. (1995) Recombinant soluble human tissue factor secreted by Saccharomyces cerevisiae and refolded from Escherichia coli inclusion bodies: glycosylation of mutants, activity and physical characterization. Biochem. J. 310(Pt2): 605-614.
Studier et al. (1990) Use of T7 RNA polymerase to direct expression of cloned genes. Meth. Enzymol. 185: 60-89.
Sugiyama et al. (2002) cDNA macroarray analysis of gene expression in synoviocytes stimulated with TNFalpha. FEBS Lett. 517(1-3): 121-128.
Taggart et al. (2003) A randomized trial of aprotinin (Trasylol) on blood loss, blood product requirement, and myocardial injury in total arterial grafting. J Thorac Cardiovasc Surg. 126(4): 1087-1094.
Takahashi et al. (1998) Regulation of matrix metalloproteinase-9 and inhibition of tumor invasion by the membrane-anchored glycoprotein RECK. Proc. Natl. Acad. Sci USA. 95(22): 13221-13226.
Tarui et al. (2002) Plasmin-induced Migration of Endothelial Cells, A Potential Target for the Anti-Angiogenic Action of Angiostatin. J. Biol. Chem. 277(37): 33564-33570.
Tatusova et al. (1999) BLAST 2 Sequences, a new tool for comparing protein and nucleotide sequences. FEMS Microbiol. Lett. 174(2): 247-250. Erratum in: FEMS Microbiol Lett. 177(1): 187-188.
Thompson et al. (1994) Clustal W: improving the sensitivity of progressive multiple sequence alignment through sequence weighting, position-specific gap penalties and weight matrix choice. Nucl. Acids Res. 22(22): 4673-4680.
Tschesche et al. (1987) Semisynthetic engineering of proteinase inhibitor homologues. Biochim. Biophys. Acta. 913(1): 97-101.
Udagawa et al. (1998) Specific expression of PP5/TFPI2 mRNA by syncytiotrophoblasts in human placenta as revealed by in situ hybridization. Placenta. 19(2-3): 217-223.
Van Nostrand et al. (1995) Enhanced Plasmin Inhibition by a Reactive Center Lysine Mutant of the Kunitz-type Protease Inhibitor Domain of the Amyloid β-Protein Precursor. J. Biol. Chem. 270(39): 22827-22830.
Wang et al. (1998) Crystal structure of the catalytic domain of human plasmin complexed with streptokinase. Science. 281(5383): 1662-1665.
Wenzel et al. (1982) Complex formation of guanidinated bovine trypsin inhibitor (Kunitz) with trypsin, chymotrypsin and trypsinogen as studied by the spin-label technique. FEBS Lett. 140(1): 53-57.
Wiedow et al. (1990) Elafin: an elastase-specific inhibitor of human skin. Purification, characterization, and complete amino acid sequence. J. Biol. Chem. 265(25): 14791-14795.
Wilder et al. (2004) The plasmin inhibitor TFPI-2/KDI blocks mononuclear cell migration into airways in a murine model of allergic asthma. Am. J. Resp. Crit. Care Med. 169(7): A803.
Winn et al. (2002) Gamma-Catenin expression is reduced or absent in a subset of human lung cancers and re-expression inhibits transformed cell growth. Oncogene. 21(49): 7497-7506.
Wlodawer et al. (1987) Comparison of two highly refined structures of bovine pancreatic trypsin inhibitor. J. Mol. Biol. 193(1): 145-156.
Wojtukiewicz et al. (2003) Immunohistochemical localization of tissue factor pathway inhibitor-2 in human tumor tissue. Thromb Haemost. 90(1): 140-146.
Wun et al. (1988) Cloning and characterization of a cDNA coding for the lipoprotein-associated coagulation inhibitor shows that it consists of three tandem Kunitz-type inhibitory domains. J. Biol. Chem. 263(13): 6001-6004.
Xu et al. (1998) The crystal structure of bikunin from the inter-alpha-inhibitor complex: a serine protease inhibitor with two Kunitz domains. J. Mol. Biol. 276(5): 955-966.

Xu et al. (2006) Tissue factor pathway inhibitor-2 is upregulated by vascular endothelial growth factor and suppresses growth factor-induced proliferation of endothelial cells. Arterioscler. Thromb.Vasc. Biol. 26: 2819-2825.
Yasim et al. (2005) Effects of topical applications of aprotinin and tranexamic acid on blood loss after open heart surgery. Anadolu Kardiyol Derg. 5(1): 36-40.
Yayoshi-Yamamoto et al. (2000) FRL, a novel formin-related protein, binds to Rac and regulates cell motility and survival of macrophages. Mol. Cell. Biol. 20(18): 6872-6881.
Zhang et al. (1999) Structure of extracellular tissue factor complexed with factor VIIa inhibited with a BPTI mutant. J. Mol. Biol. 285(5): 2089-2104.
Zhirnov et al. (2002) Cleavage of influenza a virus hemagglutinin in human respiratory epithelium is cell associated and sensitive to exogenous antiproteases. J. Virol. 76(17): 8682-8689.
Zondag et al. (2000) Receptor Protein-tyrosine Phosphatase RPTP. mu. Binds to and Dephosphorylates the Catenin p120$^{ctn}$. J. Biol Chem. 275(15): 11264-11269.
Certificate of Correction issued on Mar. 17, 2009 for U.S. Patent No. 7,432,238, U.S. Appl. No. 11/107,643, filed Apr. 15, 2008 (Inventors: Kisiel et al.).
Issue Notification issued on Sep. 17, 2008 for U.S. Patent No. 7,432,238, U.S. Appl. No. 11/107,643, filed Apr. 15, 2008 (Inventors: Kisiel et al.).
Response to Rule 1.312 Amendment issued on Aug. 8, 2008 for U.S. Patent No. 7,432,238, U.S. Appl. No. 11/107,643, filed Apr. 15, 2008 (Inventors: Kisiel et al.).
Rule 1.312 Amendment filed on Jul. 29, 2008 for U.S. Patent No. 7,432,238, U.S. Appl. No. 11/107,643, filed Apr. 15, 2008 (Inventors: Kisiel et al.).
Notice of Allowance issued on Jun. 2, 2008 for U.S. Patent No. 7,432,238, U.S. Appl. No. 11/107,643, filed Apr. 15, 2008 (Inventors: Kisiel et al.).
Response after Final Rejection filed Apr. 30, 2008 for U.S. Patent No. 7,432,238, U.S. Appl. No. 11/107,643, filed Apr. 15, 2008 (Inventors: Kisiel et al.).
Final Rejection issued Feb. 11, 2008 for U.S. Patent No. 7,432,238, U.S. Appl. No. 11/107,643, filed Apr. 15, 2008 (Inventors: Kisiel et al.).
Response after Final Rejection filed Nov. 6, 2007 for U.S. Patent No. 7,432,238, U.S. Appl. No. 11/107,643, filed Apr. 15, 2008 (Inventors: Kisiel et al.).
Non-Final Rejection issued Aug. 23, 2007 for U.S. Patent No. 7,432,238, U.S. Appl. No. 11/107,643, filed Apr. 15, 2008 (Inventors: Kisiel et al.).
Non-Final Rejection issued Mar. 28, 2007 for U.S. Patent No. 7,432,238, U.S. Appl. No. 11/107,643, filed Apr. 15, 2008 (Inventors: Kisiel et al.).
Response after Non-Final Rejection filed Jun. 5, 2007 for U.S. Patent No. 7,432,238, U.S. Appl. No. 11/107,643, filed Apr. 15, 2008 (Inventors: Kisiel et al.).
Response to Restriction Requirement filed Nov. 8, 2006 for U.S. Patent No. 7,432,238, U.S. Appl. No. 11/107,643, filed Apr. 15, 2008 (Inventors: Kisiel et al.).
Restriction Requirement issued Oct. 11, 2006 for U.S. Patent No. 7,432,238, U.S. Appl. No. 11/107,643, filed Apr. 15, 2008 (Inventors: Kisiel et al.).
Preliminary Amendment filed Nov. 16, 2005 for U.S. Patent No. 7,432,238, U.S. Appl. No. 11/107,643, filed Apr. 15, 2008 (Inventors: Kisiel et al.).
Certificate of Correction issued on Dec. 29, 2009 for U.S. Patent No. 7,585,842, U.S. Appl. No. 11/646,776, filed Dec. 28, 2006 (Inventors: Kisiel et al.).
Issue Notification issued on Aug. 19, 2009 for U.S. Patent No. 7,585,842, U.S. Appl. No. 11/646,776, filed Dec. 28, 2006 (Inventors: Kisiel et al.).
Response to Rule 1.312 Amendment issued on Jun. 24, 2009 for U.S. Patent No. 7,585,842, U.S. Appl. No. 11/646,776, filed Dec. 28, 2006 (Inventors: Kisiel et al.).
Rule 1.312 Amendment filed Jun. 18, 2009 for U.S. Patent No. 7,585,842, U.S. Appl. No. 11/646,776, filed Dec. 28, 2006 (Inventors: Kisiel et al.).

(56) References Cited

OTHER PUBLICATIONS

Notice of Allowance issued on May 21, 2009 for U.S. Patent No. 7,585,842, U.S. Appl. No. 11/646,776, filed Dec. 28, 2006 (Inventors: Kisiel et al.).
Response after Non-Final Rejection filed Apr. 28, 2009 for U.S. Patent No. 7,585,842, U.S. Appl. No. 11/646,776, filed Dec. 28, 2006 (Inventors: Kisiel et al.).
Non-Final Rejection issued Dec. 19, 2008 for U.S. Patent No. 7,585,842, U.S. Appl. No. 11/646,776, filed Dec. 28, 2006 (Inventors: Kisiel et al.).
Response to Restriction Requirement filed Oct. 22, 2008 for U.S. Patent No. 7,585,842, U.S. Appl. No. 11/646,776, filed Dec. 28, 2006 (Inventors: Kisiel et al.).
Restriction Requirement issued Sep. 22, 2008 for U.S. Patent No. 7,585,842, U.S. Appl. No. 11/646,776, filed Dec. 28, 2006 (Inventors: Kisiel et al.).
Issue Notification issued Mar. 22, 2011 for U.S. Patent No. 7,910,550, U.S. Appl. No. 12/286,933, filed Oct. 3, 2008 (Inventors: Kisiel et al.).
Corrected Notice of Allowance issued Jan. 18, 2011 for U.S. Patent No. 7,910,550, U.S. Appl. No. 12/286,933, filed Oct. 3, 2008 (Inventors: Kisiel et al.).
Notice of Allowance issued Nov. 16, 2010 for U.S. Patent No. 7,910,550, U.S. Appl. No. 12/286,933, filed Oct. 3, 2008 (Inventors: Kisiel et al.).
Response after Final Rejection filed Oct. 27, 2010 for U.S. Patent No. 7,910,550, U.S. Appl. No. 12/286,933, filed Oct. 3, 2008 (Inventors: Kisiel et al.).
Final Rejection filed Oct. 12, 2010 for U.S. Patent No. 7,910,550, U.S. Appl. No. 12/286,933, filed Oct. 3, 2008 (Inventors: Kisiel et al.).
Response after Non-Final Rejection filed Sep. 1, 2010 for U.S. Patent No. 7,910,550, U.S. Appl. No. 12/286,933, filed Oct. 3, 2008 (Inventors: Kisiel et al.).
Summary of Examiner Interview issued Aug. 19, 2010 for U.S. Patent No. 7,910,550, U.S. Appl. No. 12/286,933, filed Oct. 3, 2008 (Inventors: Kisiel et al.).
Non-Final Rejection issued Jun. 10, 2010 for U.S. Patent No. 7,910,550, U.S. Appl. No. 12/286,933, filed Oct. 3, 2008 (Inventors: Kisiel et al.).
Response to Restriction Requirement filed Feb. 18, 2011 for U.S. Appl. No. 12/269,369, filed Nov. 12, 2008 (Inventors: Kisiel et al.).
Summary of Examiner Interview issued Feb. 1, 2011 for U.S. Appl. No. 12/269,369, filed Nov. 12, 2008 (Inventors: Kisiel et al.).
Restriction Requirement issued Jan. 21, 2011 for U.S. Appl. No. 12/269,369, filed Nov. 12, 2008 (Inventors: Kisiel et al.).
Preliminary Amendment filed May 7, 2010 for U.S. Appl. No. 12/269,369, filed Nov. 12, 2008 (Inventors: Kisiel et al.).
Preliminary Amendment filed Nov. 12, 2008 for U.S. Appl. No. 12/269,369, filed Nov. 12, 2008 (Inventors: Kisiel et al.).
International Preliminary Report on Patentability issued Jul. 1, 2008 for PCT/US2006/062723 filed on Dec. 29, 2006 and published as WO 2007/076537 on Jul. 5, 2007 (Inventor: S.P. Bajaj; Applicant: Regents of the University of California).
Written Opinnion issued Dec. 12, 2007 for PCT/US2006/062723 filed Dec. 29, 2006 and later published as WO 2007/076537 on Jul. 5, 2007 (Inventor: S.P. Bajaj; Applicant: Regents of the University of California).
International Search Report issued Dec. 12, 2007 for PCT/US2006/062723 filed Dec. 29, 2006 and later published as WO 2007/076537 on Jul. 5, 2007 (Inventor: S.P. Bajaj; Applicant: Regents of the University of California).
Amended Claim Set filed Dec. 25, 2009 for Japanese Application No. 2008-548869, which claims priority to PCT/US2006/062723 filed Dec. 29, 2006 (Inventor: S.P. Bajaj; Applicant: Regents of the University of California).
Communication pursuant to Article 94(3) EPC issued Feb. 21, 2011 for European Application No. 06848474.0, which claims priority to PCT/US2006/062723 filed Dec. 29, 2006 (Inventor: S.P. Bajaj; Applicant: Regents of the University of California).
Amendment filed Nov. 3, 2010 for European Application No. 06848474.0, which claims priority to PCT/US2006/062723 filed Dec. 29, 2006 (Inventor: S.P. Bajaj; Applicant: Regents of the University of California).
Response filed Oct. 20, 2009 for European Application No. 06848474.0, which claims priority to PCT/US2006/062723 filed Dec. 29, 2006 (Inventor: S.P. Bajaj; Applicant: Regents of the University of California).
Communication pursuant to Article 94(3) issued Jun. 10, 2009 for European Application No. 06848474.0, which claims priority to PCT/US2006/062723 filed Dec. 29, 2006 (Inventor: S.P. Bajaj; Applicant: Regents of the University of California).
Response filed May 5, 2009 for European Application No. 06848474.0, which claims priority to PCT/US2006/062723 filed Dec. 29, 2006 (Inventor: S.P. Bajaj; Applicant: Regents of the University of California).
Proceeding pursuant to Rule 70(2) EPC issued Apr. 20, 2009 for European Application No. 06848474.0, which claims priority to PCT/US2006/062723 filed Dec. 29, 2006 (Inventor: S.P. Bajaj; Applicant: Regents of the University of California).
Communication issued Apr. 1, 2009 for European Application No. 06848474.0, which claims priority to PCT/US2006/062723 filed Dec. 29, 2006 (Inventor: S.P. Bajaj; Applicant: Regents of the University of California).
Response to Communication filed Oct. 1, 2008 for European Application No. 06848474.0, which claims priority to PCT/US2006/062723 filed Dec. 29, 2006 (Inventor: S.P. Bajaj; Applicant: Regents of the University of California).
Communication pursuant to Rules 161 and 162 EPC issued Aug. 29, 2008, for European Application No. 06848474.0, which claims priority to PCT/US2006/062723 filed Dec. 29, 2006 (Inventor: S.P. Bajaj; Applicant: Regents of the University of California).
Statement of Proposed Amendments filed Dec. 7, 2010 for Australian Application No. 2006330424, which claims priority to PCT/US2006/062723 filed Dec. 29, 2006 (Inventor: S.P. Bajaj; Applicant: Regents of the University of California).
Voluntary Amendment filed Apr. 7, 2009 for Canadian Patent Application No. 2,635,726, which claims priority to PCT/US2006/062723 filed Dec. 29, 2006 (Inventor: S.P. Bajaj; Applicant: Regents of the University of California).
Voluntary Amendment filed Jun. 27, 2008 for Canadian Patent Application No. 2,635,726, which claims priority to PCT/US2006/062723 filed Dec. 29, 2006 (Inventor: S.P. Bajaj; Applicant: Regents of the University of California).
UniProtKB: Q7YRQ8__dbfetch__EBI, URL=http://www.ebi.ac.uk/Tools/dbfetch/dbfetch?db= uniprot&id=q7yrq8&Submit=Go, 2003, download date Apr. 7, 2012, 2 pages.
US 7,736,867, 6/2010, Markland et al. (withdrawn).

\* cited by examiner

BPTI  RPDFCLEPPYTGPCKARI IRYFYNAKAGL CQTFVYGGCRAKRNNFKSAEDCMRTCGGA
KD-1  NAEI CLLPLDYGPCRALLLRYYYDRYTQSCRQFLYGGCEGNANNFYTWEACDDACWRI

SEQUENCE LISTING

<160> NUMBER OF SEQ ID NOS: 5

<210> SEQ ID NO 1
<211> LENGTH: 73

```
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 1

Asp Ala Ala Gln Glu Pro Thr Gly Asn Asn Ala Glu Ile Cys Leu Leu
1               5                   10                  15

Pro Leu Asp Tyr Gly Pro Cys Arg Ala Leu Leu Leu Arg Tyr Tyr Asp
                20                  25                  30

Arg Tyr Thr Gln Ser Cys Arg Gln Phe Leu Tyr Gly Gly Cys Glu Gly
            35                  40                  45

Asn Ala Asn Asn Phe Tyr Thr Trp Glu Ala Cys Asp Asp Ala Cys Trp
50                  55                  60                  65

Arg Ile Glu Lys Val Pro Lys Val
                70

<210> SEQ ID NO 2
<211> LENGTH: 73
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 2

Asp Ala Ala Gln Glu Pro Thr Gly Asn Asn Ala Glu Ile Cys Leu Leu
1               5                   10                  15

Pro Leu Asp Tyr Gly Pro Cys Arg Ala Arg Leu Leu Arg Tyr Tyr Tyr
                20                  25                  30

Asp Arg Tyr Thr Gln Ser Cys Arg Gln Phe Leu Tyr Gly Gly Cys Glu
            35                  40                  45

Gly Asn Ala Asn Asn Phe Tyr Thr Trp Glu Ala Cys Asp Asp Ala Cys
50                  55                  60

Trp Arg Ile Glu Lys Val Pro Lys Val
65                  70

<210> SEQ ID NO 3
<211> LENGTH: 59
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 3

Asn Ala Glu Ile Cys Leu Leu Pro Leu Asp Tyr Gly Pro Cys Arg Ala
1               5                   10                  15

Arg Leu Leu Arg Tyr Tyr Tyr Asp Arg Tyr Thr Gln Ser Cys Arg Gln
                20                  25                  30

Phe Leu Tyr Gly Gly Cys Glu Gly Asn Ala Asn Asn Phe Tyr Thr Trp
            35                  40                  45

Glu Ala Cys Asp Asp Ala Cys Trp Arg Ile Glu
50                  55

<210> SEQ ID NO 4
<211> LENGTH: 73
<212> TYPE: PRT
<213> ORGANISM: Artificial Sequence
<220> FEATURE:
<223> OTHER INFORMATION: Description of Artificial Sequence: Note =
```

```
           Synthetic Construct

<400> SEQUENCE: 4

Asp Ala Ala Gln Glu Pro Thr Gly Asn Asn Ala Glu Ile Cys Leu Leu
1               5                   10                  15

Pro Leu Asp Tyr Gly Pro Cys Arg Met Arg Leu Leu Arg Tyr Tyr Tyr
            20                  25                  30

Asp Arg Tyr Thr Gln Ser Cys Arg Gln Phe Leu Tyr Gly Gly Cys Glu
        35                  40                  45

Gly Asn Ala Asn Asn Phe Tyr Thr Trp Glu Ala Cys Asp Asp Ala Cys
    50                  55                  60

Trp Arg Ile Glu Lys Val Pro Lys Val
65                  70

<210> SEQ ID NO 5
<211> LENGTH: 58
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 5

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55
```

METHODS AND COMPOSITIONS RELATED TO MUTANT KUNITZ DOMAIN I OF TFPI-2

CROSS REFERENCE TO RELATED APPLICATIONS

The present application is a national phase application of International Application No. PCT/US2006/062723, filed on Dec. 29, 2006, which claims priority to U.S. Patent Application No. 60/754,731, filed Dec. 2, 2005, which application is incorporated herein fully by this reference.

STATEMENT REGARDING FEDERALLY SPONSORED RESEARCH

This invention was made with government support under HL36365 and HL70369 awarded by the National Institutes of Health. The Government has certain rights in the invention.

BACKGROUND OF THE INVENTION

The agent mainly responsible for fibrinolysis is plasmin, the activated form of plasminogen. Many substances can activate plasminogen, including activated Hageman factor, streptokinase, urokinase (uPA), tissue-type plasminogen activator (tPA), and plasma kallikrein (pKA). pKA is both an activator of the zymogen form of urokinase and a direct plasminogen activator.

Plasmin is undetectable in normal circulating blood, but plasminogen, the zymogen, is present at about 3 µM. An additional, unmeasured amount of plasminogen is bound to fibrin and other components of the extracellular matrix and cell surfaces. Normal blood contains the physiological inhibitor of plasmin, α2-plasmin inhibitor (α2-PI), at about 2 µM. Plasmin and α2-PI form a 1:1 complex. Matrix or cell bound-plasmin is relatively inaccessible to inhibition by α2-PI. Thus, activation of plasmin can exceed the neutralizing capacity of α2-PI causing a profibrinolytic state.

Plasmin, once formed, degrades fibrin clots, sometimes prematurely; digests fibrinogen (the building material of clots) impairing hemostasis by causing formation of friable, easily lysed clots from the degradation products, and inhibition of platelet adhesion/aggregation by the fibrinogen degradation products; interacts directly with platelets to cleave glycoproteins Ib and IIb/IIIa preventing adhesion to injured endothelium in areas of high shear blood flow and impairing the aggregation response needed for platelet plug formation (ADEL86); proteolytically inactivates enzymes in the extrinsic coagulation pathway further promoting a prolytic state.

Inappropriate fibrinolysis and fibrinogenolysis leading to excessive bleeding is a frequent complication of surgical procedures that require extracorporeal circulation, such as cardiopulmonary bypass, and is also encountered in thrombolytic therapy and organ transplantation, particularly liver. Other clinical conditions characterized by high incidence of bleeding diathesis include liver cirrhosis, amyloidosis, acute promyelocytic leukemia, and solid tumors. Restoration of hemostasis requires infusion of plasma and/or plasma products, which risks immunological reaction and exposure to pathogens, e.g. hepatitis virus and HIV.

Very high blood loss can resist resolution even with massive infusion. When judged life-threatening, the hemorrhage is treated with antifibrinolytics such as ε-amino caproic acid (See HOOV93) (EACA), tranexamic acid, or aprotinin (NEUH89). Aprotinin is also known as Trasylolu and as Bovine Pancreatic Trypsin Inhibitor (BPTI). Hereinafter, aprotinin will be referred to as "BPTI." EACA and tranexamic acid only prevent plasmin from binding fibrin by binding the kringles, thus leaving plasmin as a free protease in plasma. BPTI is a direct inhibitor of plasmin and is the most effective of these agents. Due to the potential for thrombotic complications, renal toxicity and, in the case of BPTI, immunogenicity, these agents are used with caution and usually reserved as a "last resort" (PUTT89). All three of the antifibrinolytic agents lack target specificity and affinity and interact with tissues and organs through uncharacterized metabolic pathways. The large doses required due to low affinity, side effects due to lack of specificity and potential for immune reaction and organ/tissue toxicity augment against use of these antifibrinolytics prophylactically to prevent bleeding or as a routine postoperative therapy to avoid or reduce transfusion therapy. Thus, there is a need for a safe antifibrinolytic.

Excessive bleeding can result from deficient coagulation activity, elevated fibrinolytic activity, or a combination of the two conditions. In most bleeding diatheses one must control the activity of plasmin. The clinically beneficial effect of bovine pancreatic trypsin inhibitor (BPTI) in reducing blood loss is thought to result from its inhibition of plasmin (Kd approximately 0.3 nM) or of plasma kallikrein (Kd approximately 100 nM) or both enzymes.

Interestingly, BPTI-induced hypersensitivity reaction occurs in about 1.2 to 2.7 percent of patients reexposed to aprotinin (30). Of these reactions 50 percent are life threatening with 9 percent fatality rate (30). Thus, a human molecule that is selectively modified to make it more potent is highly desirable. Such molecule is also expected to be less immunogenic. Side effects and toxicity issues for the use of BPTI have recently been outlined (Manago et al., N Engl J Med 2006; 354:353-65). Textilinin has also been compared with aprotinin, however, textilinin is a snake protein and therefore has immunogenecity issues associated with it. (Pathophysiol Haemost Thromb. 2005; 34(4-5):188-93 and U.S. Pat. No. 7,070,969).

What is needed in the art is a plasmin inhibitor that is as potent (or more potent) than BPTI, but that is almost identical to a human protein domain, thereby offering similar therapeutic potential but posing less potential for antigenicity.

SUMMARY OF THE INVENTION

In accordance with the purpose(s) of this invention, as embodied and broadly described herein, this invention, in one aspect, relates to a polypeptide comprising SEQ ID NO:1 with one or more mutations. For example, provided herein is SEQ ID NO:1 with one or more of the following substitutions: leucine is changed to arginine or lysine at position 17 (BPTI numbering); tyrosine is changed to glutamic acid at position 46; tyrosine is changed to threonine at position 11; aspartic acid is changed to tyrosine or glutamic acid at position 10; alanine is changed to methionine at position 16; alanine is changed to glycine at position 16; alanine is changed to serine at position 16.

Also disclosed herein are the polypeptides that inhibit plasmin. Also disclosed herein are polypeptides that inhibit plasmin and have reduced anticoagulation activity compared to the wild type Kunitz domain of TFPI-2. Also disclosed herein are polypeptides that are specific as antifibrinolytic agents.

Also disclosed are compositions comprising the polypeptides discussed herein.

Also disclosed are nucleic acids encoding the polypeptides disclosed herein.

Also disclosed are methods of inhibiting at least one activity of plasmin comprising contacting plasmin with an effective amount of a polypeptide disclosed herein.

Also disclosed is a method of treating a subject in need of inhibition of a plasmin activity, comprising administering to the subject an effective amount of a polypeptide disclosed herein. Examples of diseases, disorders, and treatments relating to the need of inhibition of plasmin include, but are not limited to, tumorogenesis, angiogenesis, bone remodeling, surgery, hemophilia, orthopedic surgery, coronary artery bypass grafting (CABG), and systemic inflammatory response syndrome (SIRS).

Also disclosed is a method of treating rheumatoid arthritis in a subject in need thereof, comprising administering to the subject an effective amount of a polypeptide disclosed herein.

Also disclosed is a method of identifying a plasmin inhibitor comprising: modeling a crystal structure of plamsin with a variant of KD1; determining interaction between the plasmin and the variant of KD1; based on results of the interaction, determining if the variant of KD1 is a plasmin inhibitor.

Also disclosed is a method of inhibiting plasmin in a subject in need thereof comprising administering to the subject an effective amount of the nucleic acid disclosed herein.

BRIEF DESCRIPTION OF THE DRAWINGS

The accompanying drawings, which are incorporated in and constitute a part of this specification, illustrate embodiments of the invention and together with the description, serve to explain the principles of the invention.

DETAILED DESCRIPTION OF THE INVENTION

Figure 1:
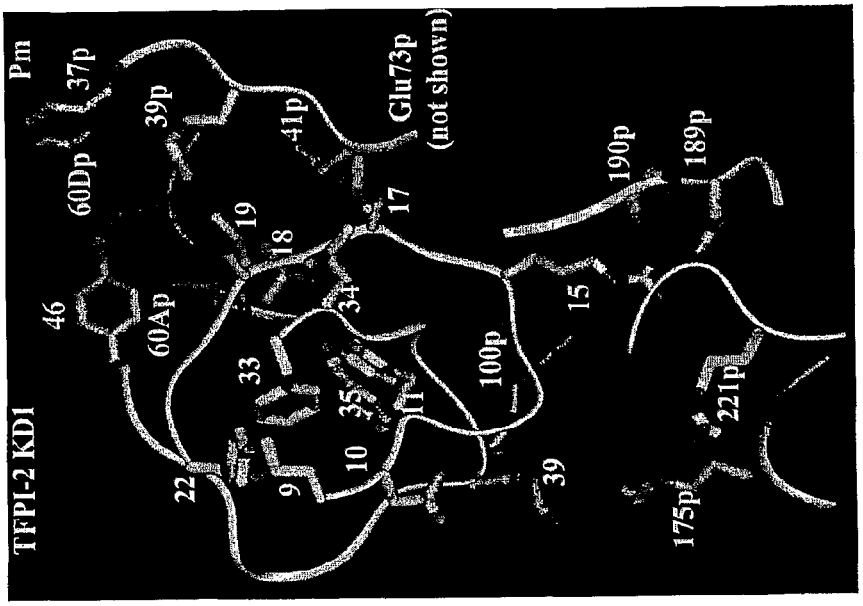
FIG. 1 shows a model of BPTI and KD1 (Kunitz domain of TFPI-2) with plasmin. Top shows the sequence alignment of BPTI (SEQ ID NO:5) KD1 (amino acids 10-67 of SEQ ID NO:1)I. Addition of 9 to the sequence will result in KD1 numbering. In the model, plasmin, BPTI and KD1 are shown as ribbons. Plasmin residues are shown with a suffix p. On the left is the BPTI:plasmin complex and on the right is the KD1:plasmin complex. Residues 9,11,22,33 and 35 both in the BPTI and KD1 form the hydrophobic core. The hydrophobic patch in BPTI as well as in KD1 comprised of residues 17, 8, 19, and 34 is shown interacting with the hydrophobic patch in plasmin consisting of residues 37 {583}, 39 {585}, and 41 {587}. Glu39 of the acidic patch in KD1 interacts directly with Arg175 {719} and possibly through water molecules to Arg100 {644} and Arg221 {767} of the basic patch in plasmin; since in BPTI residue 39 is Arg, such interactions with plasmin are not possible. Tyr46 of KD1 interacts with Lys60A {607} and Arg60D {610} in plasmin; since residue 46 is Lys in BPTI, such interactions are not possible. Arg17 in BPTI interacts with Glu73 {623} in plasmin; since residue 17 is Leu in KD1, such interaction are not possible. Thr11 in BPTI makes H-bond with the side chain N of Gln192 {738}; since residue 11 is Tyr in KD1, such interactions are not possible. Residue 192 is not shown in the figure. Also not shown is the residue 20, which is Arg in both BPTI and KD1 that interacts with the Glu60 {606} in plasmin. The P1 residue 15 in BPTI is Lys that interacts with the side chain O of Ser190 {736} and Asp189 {735} through a water molecule is shown. The P1 residue 15 in KD1 is Arg that also interacts with Ser190 and Asp189 in plasmin is shown. The numbering system used for plasmin is that of chymotrypsin. Where insertions occur, the chymotrypsin numbering is followed by a capital letter such as 60A and 60D. The numbers in curly brackets represent plasminogen numbering.
Figure 1:
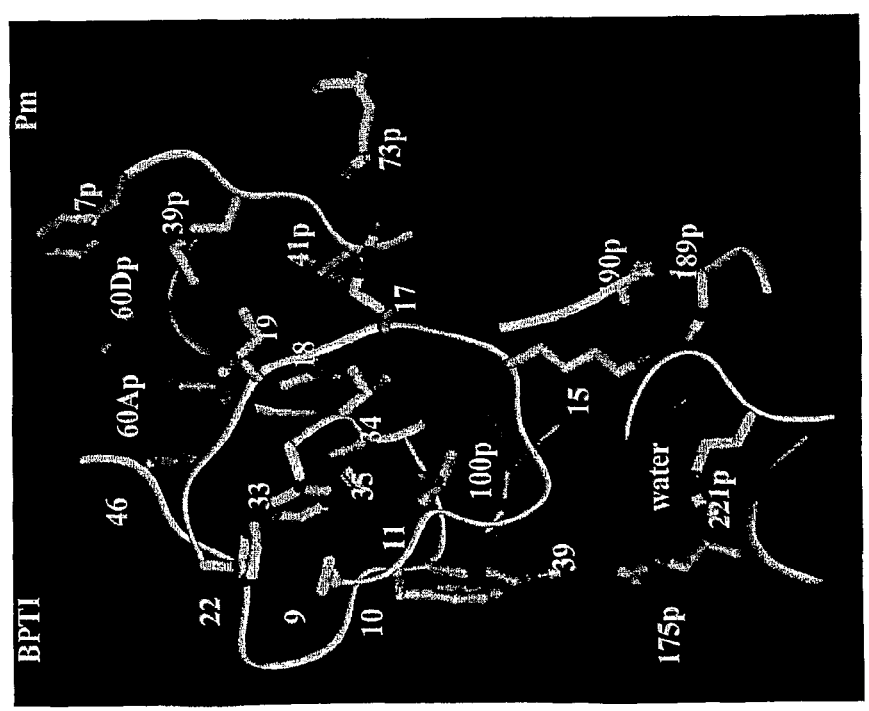

The present invention may be understood more readily by reference to the following detailed description of preferred embodiments of the invention and the examples included therein and to the figures and their previous as well as the following description.

A. Definitions

As used in the specification and the appended claims, the singular forms "a," "an" and "the" include plural referents unless the context clearly dictates otherwise. Thus, for example, reference to "a small molecule" includes mixtures of one or more small molecules, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The terms "higher," "increases," "elevates," or "elevation" refer to increases above basal levels, e.g., as compared to a control. The terms "low," "lower," "reduces," or "reduction" refer to decreases below basal levels, e.g., as compared to a control.

B. Methods of Using

Bovine pancreatic trypsin inhibitor (BPTI) is a Kunitz-type serine protease inhibitor. It inhibits plasmin and it is being used in open heart surgery and recommended in orthopaedic surgery to minimize preoperative bleeding and administration of blood products (1-5). Recently, plasminogen/plasmin system has also been implicated in development of the rheumatoid arthritis (6-10) as well as in bone remodeling and resorption (11-15) and tumorogenesis and angiogenesis (8, 16, 17).

Human tissue factor pathway inhibitor-2 (TFPI-2), also known as matrix serine protease inhibitor or placental protein 5, contains three Kunitz-type (similar to BPTI) domains in tandem with a short acidic amino terminus and very basic C-terminal tail (18,19). A variety of cells, including keratinocytes, dermal fibroblasts, smooth muscle cells, syncytiotrophoblasts, synovioblasts, and endothelial cells synthesize and secrete TFPI-2 into the extracellular matrix (ECM) (20-23). TFPI-2 is found in three forms due to differences in glycosylation with Mr 27,000, 30,000 and 32,000 (24). First Kunitz domain (KD1) of human TFPI-2 is homologous to BPTI and it also inhibits plasmin (25). Although KD1 is specific for inhibiting plasmin, the other two Kunitz domains in TFPI-2 have no discernable inhibitory activity. The C-terminal basic tail, however, may anchor TFPI-2 to the glycosamine moieties in the ECM for localized inhibition of plasmin.

The crystal structure of BPTI (26) and that of the KD1 (27) with trypsin have been determined. The crystal structure of the protease domain of human plasmin has also been determined (28). Using these structures as templates, the complexes of plasmin with BPTI as well as plasmin and KD 1 have been modeled with a high degree of accuracy. The relative positions of the inhibitors and the proteinase domain of plasmin were maintained and minor adjustments were only made in the side chains. Hydrophobic/van der Waals, hydrogen bonds, and ionic interactions were observed between each proteinase-inhibitor complex. All of these interactions were taken into consideration in evaluating each inhibitor-proteinase complex, and it was assumed that all potential hydrogen bond donors and acceptors would participate in these interactions. Bulk solvent was excluded from the proteinase-inhibitor complex and, accordingly, it was anticipated that hydrogen bonds and ionic interactions that may play an important role in specificity could be accurately evaluated. The protocols for modeling these complexes have been described earlier (29).

FIG. 1 depicts the residues in BPTI and KD1 that interacts with plasmin. From the models presented in FIG. 1, changing Leu17 to Arg, and Tyr11 to Thr in KD1 yields a molecule that has significantly higher affinity and specificity towards human plasmin. Changing Tyr46 to Glu and Asp10 to Tyr (or Glu) also increases affinity and specificity towards inhibiting plasmin. On the other hand, changing Glu39 to Arg and Tyr46 to Lys can result in substantial loss of affinity of KD1 for the human plasmin. Systematically, changing those residues that result in gain of function such as modified KD1 with Thr11 and Arg17 yields a molecule that is more potent than BPTI and native KD1. Such a molecule can also be less immunogenic than BPTI. The basic tail to the selective molecule can also be added to the C-terminal containing few extra residues as a linker such that its half-life in the extracellular matrix is increased. Herein disclosed are methods of inhibiting at least one activity of plasmin comprising contacting plasmin with an effective amount of a polypeptide disclosed herein.

Some forms of the disclosed molecules and polypeptides can inhibit plasmin but have reduced anticoagulation activity compared to the wild type Kunitz domain of TFPI-2. Some forms of the disclosed molecules and polypeptides are also specific as antifibrinolytic agents. Thus, some forms of the disclosed molecules and polypeptides are more active as antifibrinoltic agents but no longer have anticoagulant activity or have reduced anticoagulant activity. This property makes such molecules and polypeptides quite useful for preventing bleeding.

Also disclosed is a method of treating a subject in need of inhibition of a plasmin activity, comprising administering to the subject an effective amount of a polypeptide disclosed herein. Examples of diseases, disorders, and treatments relating to the need of inhibition of plasmin include, but are not limited to, tumorogenesis, angiogenesis, bone remodeling, surgery, hemophilia, orthopedic surgery, coronary artery bypass grafting (CABG), and systemic inflammatory response syndrome (SIRS).

Also disclosed is a method of treating rheumatoid arthritis in a subject in need thereof, comprising administering to the subject an effective amount of a polypeptide disclosed herein.

Also disclosed is a method of identifying a plasmin inhibitor comprising: modeling a crystal structure of plamsin with a variant of KD1; determining interaction between the plasmin and the variant of KD1; based on the interaction, determining if the variant of KD1 is a plasmin inhibitor.

Also disclosed is a method of inhibiting plasmin in a subject in need thereof comprising administering to the subject an effective amount of the nucleic acid disclosed herein.

Also disclosed is a method of showing efficacy of a compound for human use in a mouse model of reduced blood loss. It has been discovered that wild-type KD1 and the disclosed mutants both inhibit mouse plasmin (see Example 3). Thus, the mutant can be used to show efficacy in a mouse model of reduced blood loss.

Proteins of this invention may be produced by any conventional technique, including nonbiological synthesis by sequential coupling of components, e.g. amino acids, production by recombinant DNA techniques in suitable host cells, and semisynthesis, for example, by removal of undesired sequences and coupling of synthetic replacement sequences. Proteins disclosed herein are preferably produced, recombinantly, in a suitable host, such as bacteria from the genera *Bacillus, Escherichia, Salmonella, Erwinia*, and yeasts from the genera *Hansenula, Kluyveromyces, Pichia, Rhinosporidium, Saccharomyces*, and *Schizosaccharomyces*, or cultured mammalian cells such as COS-1. The more preferred hosts are microorganisms of the species *Pichia pastoris, Bacillus subtilis, Bacillus brevis, Saccharomyces cerevisiae, Escherichia coli* and *Yarrowia lipolytica*. Any promoter which is functional in the host cell may be used to control gene expression.

The proteins can be secreted and can be obtained from conditioned medium. Secretion is the preferred route because proteins are more likely to fold correctly and can be produced in conditioned medium with few contaminants. Secretion is not required.

Proteins designed to lack N-linked glycosylation sites to reduce potential for antigenicity of glycogroups can be used, and so that equivalent proteins can be expressed in a wide variety of organisms including: 1) *E. coli*, 2) *B. subtilis*, 3) *P. pastoris*, 4) *S. cerevisiae*, and 5) mammalian cells.

Several means exist for reducing the problem of host cells producing proteases that degrade the recombinant product. Overexpression of the *B. subtilis* signal peptidase in *E. coli*. leads to increased expression of a heterologous fusion protein. It has also been reported that addition of PMSF (a serine proteases inhibitor) to the culture medium improved the yield of a fusion protein.

Other factors that can affect production of these and other proteins disclosed herein include: 1) codon usage (optimizing codons for the host is preferred), 2) signal sequence, 3) amino-acid sequence at intended processing sites, presence and localization of processing enzymes, deletion, mutation, or inhibition of various enzymes that might alter or degrade the engineered product and mutations that make the host more permissive in secretion (permissive secretion hosts are preferred).

Reference works on the general principles of recombinant DNA technology include Watson et al., Molecular Biology of the Gene, Volumes I and II, The Benjamin/Cummings Publishing Company, Inc., Menlo Park, Calif. (1987); Darnell et al., Molecular Cell Biology, Scientific American Books, Inc., New York, N.Y. (1986); Lewin, Genes II, John Wiley & Sons, New York, N.Y. (1985); Old, et al., Principles of Gene Manipulation: An Introduction to Genetic Engineering, 2d edition, University of California Press, Berkeley, Calif. (1981); Sambrook et al., Molecular Cloning: A Laboratory Manual, Cold Spring Harbor Laboratory, Cold Spring Harbor, N.Y. (1989); and Ausubel et al, Current Protocols in Molecular Biology, Wiley Interscience, N.Y., (1987, 1992). These references are herein entirely incorporated by reference as are the references cited therein.

Any suitable method can be used to test the compounds of this invention. Scatchard (Ann NY Acad Sci (1949) 51:660-669) described a classical method of measuring and analyzing binding which is applicable to protein binding. This method requires relatively pure protein and the ability to distinguish bound protein from unbound.

A second appropriate method of measuring Kd is to measure the inhibitory activity against the enzyme. If the Kd to be measured is in the 1 nM to 1 µM range, this method requires chromogenic or fluorogenic substrates and tens of micrograms to milligrams of relatively pure inhibitor. For the proteins of this invention, having Kd in the range 5 nM to 50 pM, nanograms to micrograms of inhibitor suffice. When using this method, the competition between the inhibitor and the enzyme substrate can give a measured Ki that is higher than the true Ki.

A third method of determining the affinity of a protein for a second material is to have the protein displayed on a genetic package, such as M13, and measure the ability of the protein to adhere to the immobilized "second material." This method is highly sensitive because the genetic packages can be amplified. Inhibitors of known affinity for the protease are used to establish standard profiles against which other phage-displayed inhibitors are judged. Any other suitable method of measuring protein binding can also be used.

The proteins of this invention can have a Kd for plasmin of at most about 5 nM, at most about 300 pM, or 100 pM or less. The binding can be inhibitory so that Ki is the same as Kd. The Ki of QS4 for plasmin is about 2 nM. The Ki of SPI11 for plasmin is about 88 pM.

The compositions disclosed herein can be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

The compositions disclosed herein can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Effective dosages and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products.

Proteins of this invention can be applied in vitro to any suitable sample that might contain plasmin to measure the plasmin present. To do so, the assay can include a Signal Producing System (SPS) providing a detectable signal that depends on the amount of plasmin present. The signal may be detected visually or instrumentally. Possible signals include production of colored, fluorescent, or luminescent products, alteration of the characteristics of absorption or emission of radiation by an assay component or product, and precipitation or agglutination of a component or product.

The component of the SPS most intimately associated with the diagnostic reagent is called the "label". A label may be, e.g., a radioisotope, a fluorophore, an enzyme, a co-enzyme, an enzyme substrate, an electron-dense compound, or an agglutinable particle. A radioactive isotope can be detected by use of, for example, a γ counter or a scintillation counter or by autoradiography. Isotopes which are particularly useful are 3H, 125I, 131I, 35S, 14C, and, preferably, 125I. It is also possible to label a compound with a fluorescent compound. When the fluorescently labeled compound is exposed to light of the proper wave length, its presence can be detected. Among the most commonly used fluorescent labeling compounds are fluorescein isothiocyanate, rhodamine, phycoerytlrin, phycocyanin, allophycocyanin, o-phthaldehyde, and fluorescamine. Alternatively, fluorescence-emitting metals, such as 125Eu or other lanthanide, may be attached to the binding protein using such metal chelating groups as diethylenetriaminepentaacetic acid or ethylenediamine-tetraacetic acid. The proteins also can be detectably labeled by coupling to a chemiluminescent compound, such as luminol, isolumino, theromatic acridinium ester, imidazole, acridinium salt, and oxalate ester. Likewise, a bioluminescent compound, such as luciferin, luciferase and aequorin, may be used to label the binding protein. The presence of a bioluminescent protein is determined by detecting the presence of luminescence. Enzyme labels, such as horseradish peroxidase and alkaline phosphatase, are preferred.

There are two basic types of assays: heterogeneous and homogeneous. In heterogeneous assays, binding of the affinity molecule to analyte does not affect the label; thus, to determine the amount of analyte, bound label must be separated from free label. In homogeneous assays, the interaction does affect the activity of the label, and analyte can be measured without separation.

In general, a plasmin-binding protein (PBP) may be used diagnostically in the same way that an antiplasmin antibody is used. Thus, depending on the assay format, it may be used to assay plasmin, or, by competitive inhibition, other substances which bind plasmin.

The sample will normally be a biological fluid, such as blood, urine, lymph, semen, milk, or cerebrospinal fluid, or a derivative thereof, or a biological tissue, e.g., a tissue section or homogenate. The sample could be anything. If the sample is a biological fluid or tissue, it may be taken from a human or other mammal, vertebrate or animal, or from a plant. The preferred sample is blood, or a fraction or derivative thereof.

In one embodiment, the plasmin-binding protein (PBP) is immobilized, and plasmin in the sample is allowed to compete with a known quantity of a labeled or specifically labelable plasmin analogue. The "plasmin analogue" is a molecule capable of competing with plasmin for binding to the PBP, which includes plasmin itself It may be labeled already, or it may be labeled subsequently by specifically binding the label to a moiety differentiating the plasmin analogue from plasmin. The phases are separated, and the labeled plasmin analogue in one phase is quantified.

In a "sandwich assay," both an insolubilized plasmin-binding agent (PBA), and a labeled PBA are employed. The plasmin analyte is captured by the insolubilized PBA and is tagged by the labeled PBA, forming a tertiary complex. The reagents may be added to the sample in any order. The PBAs may be the same or different, and only one PBA need be a PBP according to this invention (the other may be, e.g., an antibody). The amount of labeled PBA in the tertiary complex is directly proportional to the amount of plasmin in the sample.

The two embodiments described above are both heterogeneous assays. A homogeneous assay requires only that the label be affected by the binding of the PBP to plasmin. The plasmin analyte may act as its own label if a plasmin inhibitor is used as a diagnostic reagent.

A label may be conjugated, directly or indirectly (e.g., through a labeled anti-PBP antibody), covalently (e.g., with SPDP) or noncovalently, to the plasmin-binding protein, to produce a diagnostic reagent. Similarly, the plasmin binding protein may be conjugated to a solid phase support to form a solid phase ("capture") diagnostic reagent. Suitable supports include glass, polystyrene, polypropylene, polyethylene, dextran, nylon, amylases, and magnetite. The carrier can be soluble to some extent or insoluble for the purposes of this invention. The support material may have any structure so long as the coupled molecule is capable of binding plasmin.

A Kunitz domain that binds very tightly to plasmin can be used for in vivo imaging. Diagnostic imaging of disease foci was considered one of the largest commercial opportunities for monoclonal antibodies, but this opportunity has not been achieved. Despite considerable effort, only two monoclonal antibody-based imaging agents have been approved. The disappointing results obtained with monoclonal antibodies is due in large measure to: i) inadequate affinity and/or specificity; ii) poor penetration to target sites; iii) slow clearance from nontarget sites; iv) immunogenicity; and v) high production cost and poor stability.

These limitations have led to the development of peptide-based imaging agents. While potentially solving the problems of poor penetration and slow clearance, peptide-based imaging agents are unlikely to possess adequate affinity, specificity and in vivo stability to be useful in most applications.

Engineered proteins are uniquely suited to the requirements for an imaging agent. In particular the extraordinary affinity and specificity that is obtainable by engineering small, stable, human-origin protein domains having known in vivo clearance rates and mechanisms combine to provide earlier, more reliable results, less toxicity/side effects, lower production and storage cost, and greater convenience of label preparation. Indeed, it is possible to achieve the goal of real-time imaging with engineered protein imaging agents. Plasmin-binding proteins, e.g. SPI11, can be useful for localizing sites of internal hemorrhage.

Radio-labeled binding protein may be administered to the human or animal subject. Administration is typically by injection, e.g., intravenous or arterial or other means of administration in a quantity sufficient to permit subsequent dynamic and/or static imaging using suitable radio-detecting devices. The dosage is the smallest amount capable of providing a diagnostically effective image, and may be determined by means conventional in the art, using known radio-imaging agents as guides.

Typically, the imaging is carried out on the whole body of the subject, or on that portion of the body or organ relevant to the condition or disease under study. The radio-labeled binding protein has accumulated. The amount of radio-labeled binding protein accumulated at a given point in time in relevant target organs can then be quantified.

A particularly suitable radio-detecting device is a scintillation camera, such as a γ camera. The detection device in the camera senses and records (and optional digitizes) the radioactive decay. Digitized information can be analyzed in any suitable way, many of which are known in the art. For example, a time-activity analysis can illustrate uptake through clearance of the radio-labeled binding protein by the target organs with time.

Various factors are taken into consideration in picking an appropriate radioisotope. The isotope is picked: to allow good quality resolution upon imaging, to be safe for diagnostic use in humans and animals, and, preferably, to have a short half-life so as to decrease the amount of radiation received by the body. The radioisotope used should preferably be pharmacologically inert, and the quantities administered should not have substantial physiological effect. The binding protein may be radio-labeled with different isotopes of iodine, for example 123I, 125I, or 131I (see, for example, U.S. Pat. No. 4,609,725). The amount of labeling must be suitably monitored.

In applications to human subjects, it may be desirable to use radioisotopes other than 125I for labeling to decrease the total dosimetry exposure of the body and to optimize the detectability of the labeled molecule. Considering ready clinical availability for use in humans, preferred radio-labels include: 99mTc, 67Ga, 68Ga, 90Y, 111In, 113mIn, 123I, 186Re, 188Re or 211At. Radio-labeled protein may be prepared by various methods. These include radio-halogenation by the chloramine-T or lactoperoxidase method and subsequent purification by high pressure liquid chromatography, for example, see Gutkowska et al in "Endocrinology and Metabolism Clinics of America: (1987) 16(1): 183. Other methods of radio-labeling can be used, such as IODO-BEADS™.

A radio-labeled protein may be administered by any means that enables the active agent to reach the agent's site of action in a mammal. Because proteins are subject to digestion when administered orally, parenteral administration, i.e., intravenous subcutaneous, intramuscular, would ordinarily be used to optimize absorption.

The plasmin-binding proteins of this invention may also be used to purify plasmin from a fluid, e.g., blood. For this purpose, the PBP is preferably immobilized on an insoluble support. Such supports include those already mentioned as useful in preparing solid phase diagnostic reagents.

Proteins can be used as molecular weight markers for reference in the separation or purification of proteins. Proteins may need to be denatured to serve as molecular weight markers. A second general utility for proteins is the use of hydrolyzed protein as a nutrient source. Proteins may also be used to increase the viscosity of a solution.

The protein of this invention may be used for any of the foregoing purposes, as well as for therapeutic and diagnostic purposes as discussed further earlier in this specification.

Chemical polypeptide synthesis is known in the art, and methods of solid phase polypeptide synthesis are well-described in the following references, hereby entirely incorporated by reference: (Merrifield, J Amer Chem Soc 85:2149-2154 (1963); Merrifield, Science 232:341-347 (1986); Wade et al., Biopolymers 25:S21-S37 (1986); Fields, Int J Polypeptide Prot Res 35:161 (1990); MilliGen Report Nos. 2 and 2a, Millipore Corporation, Bedford, Mass., 1987) Ausubel et al, supra, and Sambrook et al, supra. Tan and Kaiser (Biochemistry, 1977, 16:1531-41) synthesized BPTI and a homologue eighteen years ago.

As is known in the art, such methods involve blocking or protecting reactive functional groups, such as free amino, carboxyl and thio groups. After polypeptide bond formation, the protective groups are removed. Thus, the addition of each amino acid residue requires several reaction steps for protecting and deprotecting. Current methods utilize solid phase synthesis, wherein the C-terminal amino acid is covalently linked to insoluble resin particles that can be filtered. Reactants are removed by washing the resin particles with appropriate solvents using an automated machine. Various methods, including the "tBoc" method and the "Fmoc" method are well known in the art. See, inter alia, Atherton et al., J Chem Soc Perkin Trans 1:538-546 (1981) and Sheppard et al, Int J Polypeptide Prot Res 20:451-454 (1982).

C. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that, while specific reference of each various individual and collective combinations and permutation of these compounds may not be explicitly disclosed, each is specifically contemplated and described herein. For example, if a particular amino acid sequence is disclosed and discussed and a number of modifications that can be made to a number of places within the sequence can be made are discussed, specifically contemplated is each and every combination and permutation of the amino acid and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed herein is a polypeptide comprising SEQ ID NO:1 (Kunitz Type Domain 1, or KD1). SEQ ID NO: 1 is represented by the following: DAAQEPTGNNAEICLLPLD YGPCRALLLRYYYDR YTQSCRQFLYGGCEGNANN-FYTWEACDDACWRIEKVPKV.

Also disclosed are polypeptides comprising SEQ ID NO:2 (wherein the leucine at position 17 as numbered in BPTI has been changed to arginine): DAAQEPTGNNAEICLL PLDYGPCRARLLRYYYDRYTQSCRQ-FLYGGCEGNANNFYTWEACDDACWRIEKV PKV.

Also disclosed is SEQ ID NO:3, which is a shorter polypeptide than SEQ ID NO: 1, and also comprises the change at position 17 (L17R): NAEICLLPLDYGPCRAR LLRYYYDRYTQSCRQFLYGGCEGNANN-FYTWEACDDACWRIE.

Also disclosed are polypeptides comprising SEQ ID NO:4 (wherein the leucine at position 17 as numbered in BPTI has been changed to arginine and the alanine at position 16 has been changed to methionine): DAAQEPTGNNAEICLL-PLDYGPC RMRLLRYYYDRYTQSCRQFLYGGCEG-NANNFYTWEACDDACWRIEKVPKV.

It has been discovered that a change from the hydrophobic amino acid at position 17 (leucine) to a charged amino acid such as arginine or lysine affects the anticoagulation activity of KD1 without significantly reducing plasmin inhibition. Particularly useful are such mutant polypeptides where anticoagulation activity is eliminated and plasmin inhibition is increased. Thus, inclusion of a charged or polar amino acid at position 17 is specifically contemplated herein.

The polypeptide of SEQ ID NO:1 can also comprise one or more additional mutations. As disclosed herein, a mutation can be an addition, deletion, or substitution of an amino acid. For example, in addition to the change of leucine to arginine at position 17, the amino acid sequence can also comprise the change of arginine to lysine at position 15, the change of alanine to methionine at position 16, or both. Examples of other changes at position 15 can be found, for example, in U.S. Pat. No. 4,595,674, herein incorporated by reference in its entirety.

Also disclosed herein is a polypeptide comprising SEQ ID NO:1, wherein tyrosine is changed to glutamic acid at position 46. In another embodiment, tyrosine can be changed to threonine at position 11. In another embodiment, aspartic acid can be changed to tyrosine or glutamic acid at position 10. These polypeptides can also comprise one or more additional mutations, such as those discussed above. To summarize, examples of amino acid changes to SEQ ID NO:1 can be found in Table 1. These are only examples, and one of skill in the art would understand that any of these mutations could be used alone or in combination with the other mutations listed herein, or with others not listed, in any permutation or combination possible.

TABLE 1

Mutations of SEQ ID NO: 1

L17R

L17K

D10Y

D10E

Y11T

Y46E

A16G

A16M

A16S

Also disclosed are compositions and nucleic acids corresponding to the polypeptides discussed herein. A discussion of nucleic acids, compositions, and methods of administration is below. Also disclosed are nucleic acids encoding the polypeptides disclosed herein. Disclosed herein are polypeptides and their corresponding nucleic acids. It is understood that one way to define any known variants and derivatives or those that might arise of the disclosed nucleic acids and proteins herein is through defining the variants and derivatives in terms of homology to specific known sequences. For example SEQ ID NO:1 sets forth a particular sequence of KD1, and SEQ ID NO:2 sets forth a particular sequence of KD1 containing a mutation. One of ordinary skill in the art at the time of the invention would have understood that other mutations can occur in both the nucleic acid and the protein of the wild type. Some mutations thereof that would not affect its functionality, while others can affect the functionality in a positive way, and are therefore selected for. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. There are molecules disclosed herein that are nucleic acid based, including for example the nucleic acids that encode, for example, KD1 as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556).

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

There are a variety of sequences related to, for example, KD1 and mutations thereof, as well as any other protein disclosed herein that are disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

Disclosed herein are methods of treating a subject comprising administering to the subject in need thereof a nucleic acid. For example, disclosed herein are methods of delivering a nucleic acid encoding a mutant of KD1, such as those disclosed herein. These methods include the administration and uptake of exogenous DNA into the cells of a subject (i.e., gene transduction or transfection). The disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., Proc. Natl. Acad. Sci. U.S.A. 85:4486, 1988; Miller et al., Mol. Cell. Biol. 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., Hum. Gene Ther. 5:941-948, 1994), adeno-associated viral (AAV) vectors (Goodman et al., Blood 84:1492-1500, 1994), lentiviral vectors (Naidini et al., Science 272:263-267, 1996), pseudotyped retroviral vectors (Agrawal et al., Exper. Hematol. 24:738-747, 1996). Physical transduction techniques can also be used, such as liposome delivery and receptor-mediated and other endocytosis mechanisms (see, for example, Schwartzenberger et al., Blood 87:472-478, 1996). This disclosed compositions and methods can be used in conjunction with any of these or other commonly used gene transfer methods.

As one example, if the antibody-encoding nucleic acid is delivered to the cells of a subject in an adenovirus vector, the dosage for administration of adenovirus to humans can range from about 107 to 109 plaque forming units (pfu) per injection but can be as high as 1012 pfu per injection (Crystal, Hum. Gene Ther. 8:985-1001, 1997; Alvarez and Curiel, Hum. Gene Ther. 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., Remington: The Science and Practice of Pharmacy (19th ed.) ed. A. R. Gennaro, Mack Publishing Company, Easton, Pa. 1995.

As discussed herein there are numerous variants of the KD1 protein that are known and herein contemplated. Specifically, disclosed are mutations of KD1 that are preferable in view of the wild type, such as SEQ ID NO:2. In addition to the functional KD1 variants disclosed herein, there are derivatives of the KD1 protein which also function with those disclosed herein, and are herein contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table and are referred to as conservative substitutions.

TABLE 2

Amino Acid Substitutions Original Residue Exemplary Conservative Substitutions, others are known in the art.

| | |
|---|---|
| Ala; | ser |
| Arg; | lys, gln |
| Asn; | gln; his |
| Asp; | glu |
| Cys; | ser |
| Gln; | asn, lys |
| Gln; | asp |
| Gly; | pro |
| His; | asn; gln |
| Ile; | leu; val |
| Leu; | ile; val |
| Lys; | arg; gln |
| Met; | leu; ile |
| Phe; | met; leu; tyr |
| Ser; | thr |
| Thr; | ser |
| Trp; | tyr |
| Tyr; | trp; phe |
| Val; | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO:1 sets forth a particular sequence of KD1, and SEQ ID NO:2 sets forth a particular sequence of a mutant thereof. Specifically disclosed are variants of these and other proteins herein disclosed which have at least 70% or 75% or 80% or 85% or 90% or 95% homology to the stated sequence. Those of skill in the art readily understand how to determine the homology of two proteins. For example, the homology can be calculated after aligning the two sequences so that the homology is at its highest level. Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular region from which that protein arises is also known and herein disclosed and described.

It is understood that there are numerous amino acid and peptide analogs which can be incorporated into the disclosed compositions. For example, there are numerous D amino acids or amino acids which have a different functional substituent than those shown in Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way. See, for example, (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include CH2NH—, —CH2S—, —CH2-CH2-, —CH═CH— (cis and trans), —COCH2-, —CH(OH)CH2-, and —CHH2SO— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH2NH—, CH2CH2-); Spatola et al. Life Sci 38:1243-1249 (1986) (—CH H2-S); Hann J. Chem. Soc Perkin Trans. I 307-314 (1982) (—CH—CH—, cis and trans); Almquist et al. J. Med. Chem. 23:1392-1398 (1980) (—COCH2-); Jennings-White et al. Tetrahedron Lett 23:2533 (1982) (—COCH2-); Szelke et al. European Appln, EP 45665 CA (1982): 97:39405 (1982) (—CH(OH)CH2-); Holladay et al. Tetrahedron. Lett 24:4401-4404 (1983) (—C(OH)CH2-); and Hruby Life Sci 31:189-199 (1982) (—CH2-S—); each of which is incorporated herein by reference. A particularly preferred non-peptide linkage is —CH2NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Disclosed are methods of making a transgenic organism comprising administering the disclosed nucleic acids, vectors and/or cells.

The present invention is more particularly described in the following examples, which are intended as illustrative only since numerous modifications and variations therein will be apparent to those skilled in the art.

Although the present process has been described with reference to specific details of certain embodiments thereof, it is not intended that such details should be regarded as limitations upon the scope of the invention except as and to the extent that they are included in the accompanying claims.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

D. Examples

1. Example 1

Materials and methods: The chromogenic substrates H-D-Val-Leu-Lys-p-nitroanilide (S-2251) was purchased from DiaPharma Group Inc. (West Chester, Ohio). Human plasmin was purchased from Enzyme research laborotories. Bovine aprotinin (BPTI) was used from Zymogenetics. *Escherichia coli* strain BL21(DE3)pLys and pET28a expression vector were products of Novagen Inc. (Madison, Wis.). The QuikChange® site-directed mutagenesis kit was obtained from Stratagene (La Jolla, Calif.).

Expression and Purification of Wild type and Mutant Proteins. The first Kunitz-type proteinase inhibitor domain of human TFPI-2 (KD1) was cloned into pET28a vector containing a His tag. The mutants were obtained by site directed mutagenesis. The proteins were overexpressed as N-terminal His-tagged fusion proteins in *E. coli* strain BL21(DE3) pLys S. using the T7 promoter system. The overexpressed proteins were recovered as inclusion bodies and proteins were folded and purified free of his Tag (27). The concentrations were determined by UV spectroscopy.

Plasmin Inhibition Assays. Plasmin inhibition assays were performed by incubating plasmin with various concentrations of inhibitor preparations (BPTI, KD1WT, KD1 mutants R24K, L26R or R24K/L26R) in 50 mM Tris-HCl, pH 7.5 containing 100 mM NaCl, 0.1 mg/mL BSA, 5 mM CaCl2 for 1 hr at 37° C. in a 96-well microtitre plate. The chromogenic substrate S-2251 was then added, and residual amidolytic activity was measured in a Molecular Devices UVmax kinetic microplate reader at different end points (0.5 and 1 hr) and S2251 (0.5 and 1 mM) concentrations. Plasmin inhibitory data were analyzed according to the quadratic binding expression.

Figure 2:
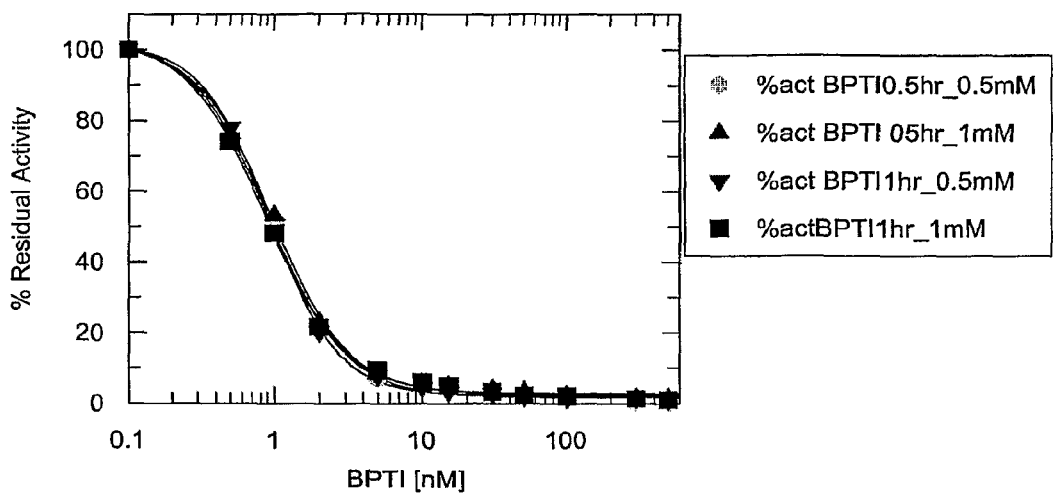
FIG. 2 shows control experiments showing Inhibition of Plasmin by BPTI at different times (0.5 & 1 hr) and substrate (S-2251) concentrations (0.5 & 1 mM). BPTI binds plasmin with an apparent dissociation constant Kd of 1±0.5). Also there does not seem to be any substrate-induced displacement of the bound inhibitor.
Figure 3:
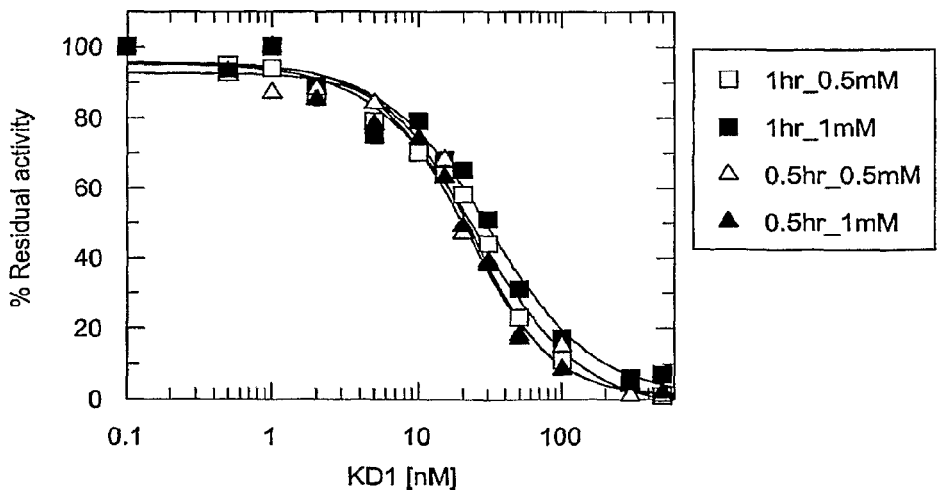
FIG. 3 shows inhibition of plasmin by WTKD1 at different times (0.5 and 1 hr) and substrate concentrations (0.5 and 1 mM) WTKD1 binds plasmin with an apparent Kd of 22±2 nM. Also there is not any significant substrate induced displacement of inhibitor.
Figure 4:
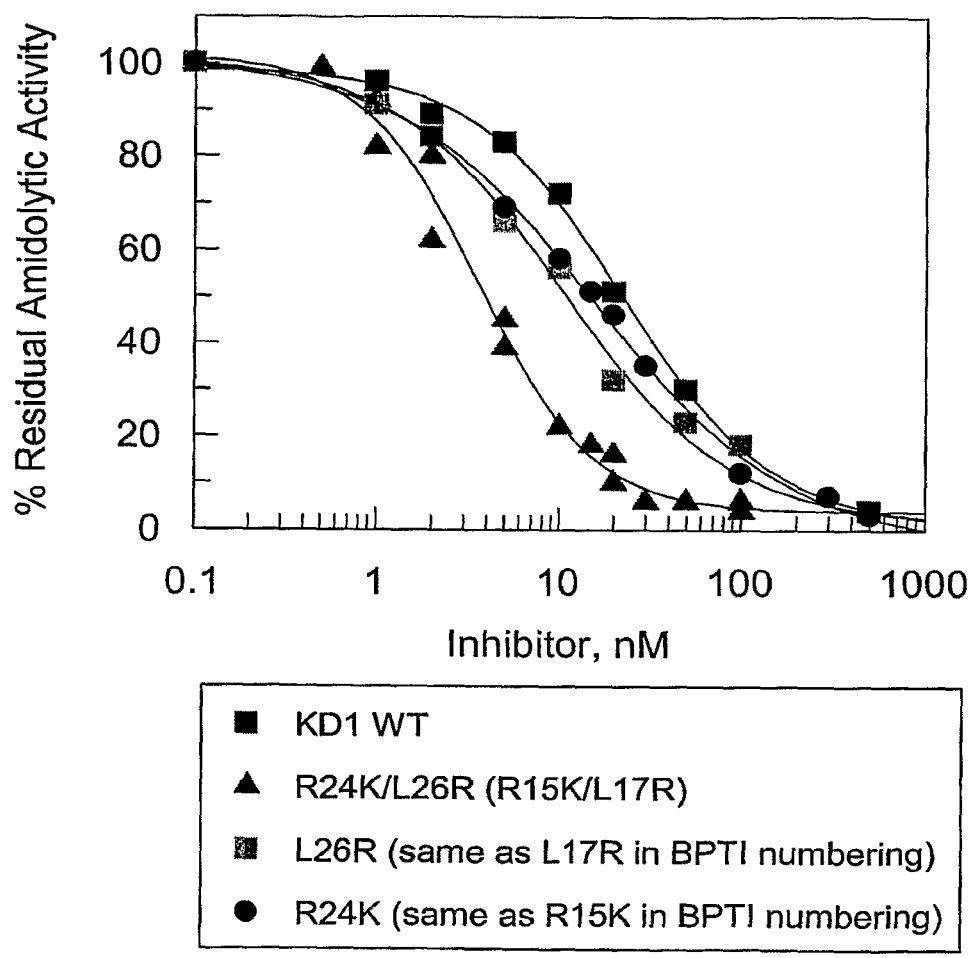
FIG. 4 shows inhibition of plasmin by WTKD1, R15K/L17R and R15K (note that in the figures, R24K=R15K and L26R=L17R, where R24K and L26R are KD1 numbering, and R15K and L26R are BPTI numbering). The incubation time was 1 hr at 37° C. and substrate concentration was 1 mM for the remaining activity measurements. The R15K/L17R mutant inhibits plasmin with an apparent Kd of 3±1 nM. The R24K mutant inhibits plasmin with a Kd of 9-11 nM. The WT KD1 inhibits plasmin with a Kd of 22 nM, which is two-fold different from the Kd of 10±2 nM for the R24K mutant. The L26R (L17R in BPTI numbering) gave KD value of 6±2, which is ~4-fold better than the WT KD1.

In control experiments, it was first studied if there was any substrate-induced displacement of bound inhibitor by increasing substrate concentrations. Both BPTI (FIG. 2) and WTKD1 (FIG. 3) were assayed and our results show that there is apparently no displacement of bound inhibitor by increasing substrate concentrations. It was also tested whether or not increased time of incubation of inhibitor with plasmin would result in enhanced inhibition. This was not the case either (FIG. 2 and FIG. 3). These results validate the results presented in FIG. 4. The results obtained from the plasmin inhibitory studies show that the mutant R15K/L17R is a potent inhibitor of plasmin and inhibits plasmin manifold strongly than either the wild type KD1 or the R24K mutant (FIG. 4). Ki* (inhibitory constant) values of 22 nM for WT, 10 nM for R15K, 6 nM for L26R and 3 nM for the R15K/L17R were obtained. Thus L17R change is very important. The L17R change was made based upon molecular modeling. The R15K/L17R mutant binds much strongly to plasmin than WTKDI (7-fold) or the R15K (~2-fold) mutant. The L17R mutants binds plasmin approximately 4-fold stronger than the WT KD1 Thus, L26R or R15K/L17R can replace BPTI in clinical therapeutics.

Throughout this application, various publications are referenced. The disclosures of these publications in their entireties are hereby incorporated by reference into this application in order to more fully describe the state of the art to which this invention pertains.

2. Example 2

Abolishing the Intrinsic Coagulation Inhibitor Activity of Kunitz Domain 1 (KD1) of TFPI-2

Nomenclature Information
R24 (also known as R15) is P1
A25 (also known as A16) is P1'
L26 (also known as L17) is P2'

TFPI-2 inhibits intrinsic coagulation presumably through the inhibition of factor XIa (Petersen et al. Biochemistry. 1996 Jan. 9; 35(1):266-272). Like all serine proteases, factor XIa cleaves between P1-P1' residues TRAE or TRW (P2-P1-P1'-P2'). Thus KD1 WT having Leu (hydrophobic residue like Val) at P2' position should inhibit factor XIa. Thus changing Leu to Arg at P2' position should reduce/abrogate this inhibition.

Figure 5:
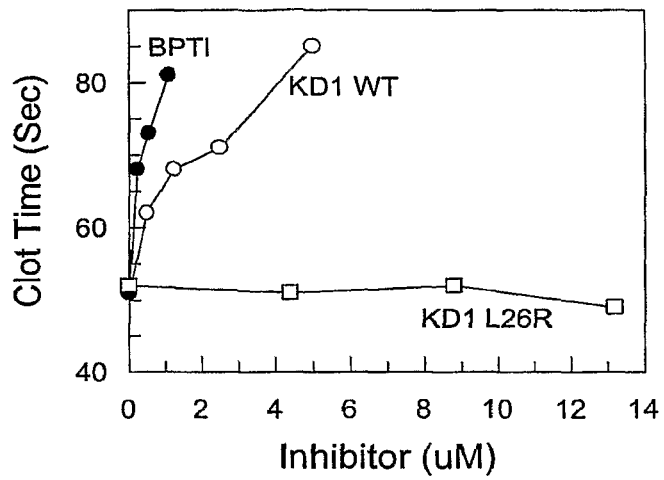
FIG. 5 shows an example wherein surface activator plus phospholipid was mixed with normal human plasma in equal amounts (75 microliter). Ten microliter of buffer containing inhibitor (KD1 wt, KD1 L26R or BPTI) was added and the sample incubated for five minutes at 37° C. Seventy-five microliter of 25 mM CaCl$_2$ prewarmed to 37° C. was then added and the time needed to form the clot through the intrinsic pathway of blood coagulation was noted. The data show that KD1 WT and BPTI each inhibit the intrinsic pathway of coagulation whereas L26R mutant (L17R in BPTI numbering) of KD1 is ineffective in this regard. Similarly, the extrinsic pathway of coagulation is expected not to be inhibited by the L26R change.

A common procedure to test inhibition of clotting is to examine the aPTT (activated partial thromboplastin time) of normal plasma. In this test, surface activator plus phospholipid was mixed with normal plasma in equal amounts (75 microliter). Ten microliter of buffer containing inhibitor (KD1 wt, KD1 L26R or BPTI) was added and the sample incubated for five minutes at 37° C. Seventy-five microliter of 25 mM CaCl$_2$ prewarmed to 37° C. was then added and the time needed to form the clot was noted. The data are shown in FIG. 5.

In the aPTT system, coagulation is initiated by the activation of factor XII to Factor XIIa by contact phase involving the kallikrein system. Factor XIIa then activates factor XI to factor XIa in the coagulation cascade.

BPTI inhibits kallikrein whereas KD1 WT inhibits both kallikrein and factor XIa (Petersen et al 1996). This can result in the prolongation of the aPTT by BPTI and KD1 WT whereas L26R Mutant of KD1 is expected to inhibit neither as indicated by no inhibition (prolongation) of aPTT (FIG. 5). This observation makes the L26R KD1 a specific inhibitor of plasmin. It also increases its inhibitory potency towards plasmin as well. Thus, L26R KD1 has no effect on clotting and is a more potent inhibitor than the Wt KD1.

The mutant protein L26R loses activity as an anticoagulant and becomes specific as an antifibrinolytic agent. So the mutant is more active as an antifibrinoltic agent but it also is no longer an anticoagulant. This property makes it useful in preventing bleeding.

3. Example 3

Mouse Plasmin Inhibition Data

Figure 6:
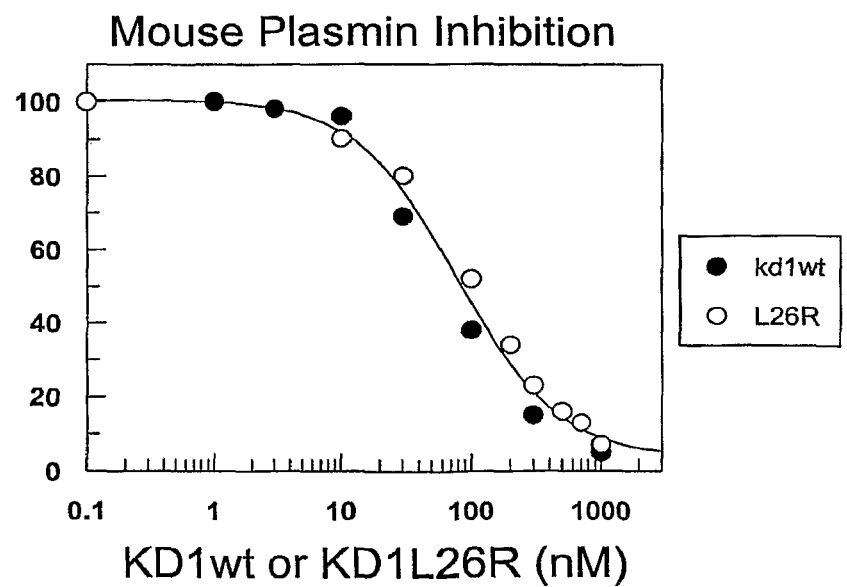
FIG. 6 shows both wt KD 1 and L26R inhibited mouse plasmin effectively. The WtKd1 and the L26R mutant are quite effective in inhibiting mouse plasmin with an apparent KD value of ~80 nM. Complete inhibition was obtained at 1 μM for both wt and L26R KD1.

Both WT KD1 and L26R inhibited mouse plasmin effectively. This is shown in FIG. 6. Clearly the WT KD1 and the L26R mutant are quite effective in inhibiting mouse plasmin with an apparent Kd value of ~80 nM. Complete inhibition was obtained at 1 µM for both WT and L26R KD1 (Masci et al. Blood Coagulation and Fibrinolysis 2000, Vol 11, No 4, pages 385-393, reference herein incorporated in its entirety and for its teachings regarding in vivo plasmin inhibition). Since both the wild-type and the mutant inhibit mouse plasmin, one can use the mutant to show efficacy in vivo in an animal model of bleeding.

A mouse tail vein bleeding model has been described to study the efficacy of a snake plasmin inhibitor (Masci et al. Blood Coagulation and Fibrinolysis 2000, Vol 11, pages 385-393). Using this mouse tail vein bleeding model, compared to saline control, a 67-70% reduction in blood loss was observed when either Aprotinin, WT KD1 or the mutant L26R was administered intravenously at about 100 microgram/mouse. The doses of the plasmin inhibitors used in these experiments were similar to that used during human CPB (cardiopulmonary bypass) surgery, adjusted to the mouse weight. The Animal Ethics Committee of UCLA approved all mice experiments and the dose used in human surgery adjusted to mouse weight was a realistic basis for these initial studies. The serum BUN/Creatinine levels were normal after two days and seven days following administration of the drug. The microscopic examination of tissues revealed no injury to major organs such as kidney, heart and brain. KD1 WT and KD1 L26R reduced blood loss nearly as effectively as Aprotinin. However, this is expected since the dose used may be high enough to not see differences between the different inhibitors (aprotinin, WT KD1 or the L26R mutant). Further the human KD1 L26R could have a better efficacy in humans because it inhibits human plasmin more selectively and does not inhibit coagulation.

REFERENCES

1. Gans H, Castaneda A R, Subramanian V, John S, Lillehei C W. Problems in hemostasis during open heart surgery. IX. Changes observed in the plasminogen-plasmin system and their significance for therapy. *Ann Surg* 166: 980-986, 1967.
2. Shahian D M, and Levine J D. Open-heart surgery in a patient with heterozygous alpha 2-antiplasmin deficiency. Perioperative strategies in the first reported case. *Chest* 97:1488-1490, 1990.

3. Taggart D P, Diapardy V, Naik M, and Davies A. A randomized trial of aprotinin (Trasylol) on blood loss, blood product requirement, and myocardial injury in total arterial grafting. *J Thorac Cardiovasc Surg* 126: 1087-94, 2003.
4. Sievert A, McCall M, Blackwell M, and Bradley S. Effects of topical applications of aprotinin and tranexamic acid on blood loss after open heart surgery. *Anadolu Kardiyol Derg.* 5:3640, 2005
5. Kokoszka A, Kuflik P, Bitan F, Casden A, Neuwirth M. Evidence-based review of the role of aprotinin in blood conservation during orthopaedic surgery. *J Bone Joint Surg Am* 87:1129-36, 2005
6. Li J, Ny A, Leonardsson, G, Nandakumar K S, Holmdahl R., and Ny T. The plasminogen activator/plasmin system is essential for development of the joint inflammatory phase of collagen type II-induced arthritis. *Am J Pathol* 166: 783-92, 2005.
7. Judex M O, and Mueller B M. Plasminogen activation/ plasmin in rheumatoid arthritis: matrix degradation and more. *Am J Pathol* 166: 645-647, 2005
8. Lijnen H R. Pleiotropic functions of plasminogen activator inhibitor-1. J Thromb Haemost 1:3545, 2005
9. Hilal G, Martel-Pelletier J, Pelletier J P, Ranger P, and Lajeunesse D., Osteoblast-like cells from human subchondral osteoarthritic bone demonstrate analtered phenotype in vitro. Possible role in subchondral bone sclerosis. *Arthritis Rheum* 41:891-899, 1998
10. Ronday H K, Smits H H, Quax P H, van der Pluijm G, Lowik C W, Breedveld F C, and Verheijen J H. Bone matrix degradation by the plasminogen activation system. Possible mechanism of bone destruction in arthritis. *Br J Rheumatol* 36:9-15, 1997.
11. Novak J F, Hayes J D, Nishimoto S K. Plasmin-mediated proteolysis of osteocalcin. *J Bone Miner Res* 12:1035-1042, 1997.
12. Daci E, Udagava N, Martin T J, Bouillon R, and Carmeliet G. The role of the plasminogen system in bone resorption in vitro. *J Bone Miner Res* 14:946-52, 1999
13. Sakamaki H, Ogura N, Kujiraoka H, Akiba, M, Abikao Y, and Nagura H. Activities of plasminogen activator, plasmin and kallikrein in synovial fluid from patients with temporomandibular joint disorders. *Int J Oral Maxillofac Surg* 30:323-328, 2001
14. Roy M E, Nishimoto S K. Matrix Gla protein binding to hydroxyapatite is dependent on the ionic environment: calcium enhances binding affinity but phosphate and magnesium decrease affinity. *Bone* 31:296-302, 2002.
15. Daci E. Everts V, Torrekens S, Van Herck E, Tigchelaar-Gutterr W, Bouillon R, and Carmeliet G. Increased bone formation in mice lacking plasminogen activators. *J Miner Res Bone* 18:1167-76, 2003.
16. Choong P F, and Nadesapillai. Urokinase plasminogen activator system: a multifunctional role in tumor progression and metastasis. *Clin Orthop Relat Res* 415:S46-S58, 2003 (Suppl)
17. Castellino F J, and Ploplis V A. Structure and function of the plasminogen/plasmin system. *Thromb Haemost* 93:647-54, 2005
18. Sprecher C A, Kisiel W, Mathewes S, and Foster D C. Molecular cloning, expression, and partial characterization of a second human tissue factor pathway inhibitor. *Proc Natl Acad Sci USA* 91:3353-7, 1994
19. Miyagi Y, Koshikawa N, Yasumitsu H, Miyagi E, Hirahara F, Aoki I, Misugi K, Umeda M, and Miyazaki K. cDNA cloning and mRNA expression of a serine proteinase inhibitor secreted by cancer cells: identification as placental protein 5 and tissue factor pathway inhibitor-2. *J Biochem* (Tokyo) 116:939-42, 1994
20. Rao C N, Peavey C L, Liu Y Y, Lapiere J C, and Woodley D T. Partial characterization of matrix-associated serine protease inhibitors from human skin cells *J Invest. Dermatol.* 104, 379-383, 1995
21. Udagawa K, Miyagi Y, Hirahara F, Miyagi E, Nagashima, Y, Minaguchi H, Misugi K, Yasumitsu H, and Miyazali K. Specific expression of PP5/TFPI2 mRNA by syncytiotrophoblasts in human placenta as revealed by in situ hybridization *Placenta* 19, 217-223, 1998
22. Sugiyama T, Ishii S, Yamamoto J, Irie R, Saito K, Otuki T, Wakamatsu A, Suzuki Y, Hio Y, Ota T, Nishikawa T, Sugano S, Masuho Y, Isogai T. cDNA macroarray analysis of gene expression in synoviocytes stimulated with TNFalpha *FEBS Lett.* 517, 121-128, 2002
23. Iino M, Foster D C, Kisiel W. Quantification and characterization of human endothelial cell-derived tissue factor pathway inhibitor-2. *Arterioscler. Thromb. Vasc. Biol.* 18, 40-46, 1998
24. Rao C N, Reddy P, Liu Y Y, O'Toole E A O, Reeder D J, Foster D C, Kisiel W, and Woodley, D T. Extracellular matrix-associated serine protease inhibitors (Mr 33,000, 31,000, and 27,000) are single-gene products with differential glycosylation: cDNA cloning of the 33-kDa inhibitor reveals its identity to tissue factor pathway inhibitor-2. *Arch. Biochem. Biophys.* 335, 45-52, 1996
25. Chand, H. S., Schmidt, A. E., Bajaj, S. P., and Kisiel, W. Structure-function analysis of the reactive site in the first Kunitz-type domain of human tissue factor pathway inhibitor-2. *J Biol Chem* 279:17500-17507, 2004
26. Huber R, Kukla D, Bode W, Schwager P, Bartels K, Deisenhofer J, Steigemann W. Structure of the complex formed by bovine trypsin and bovine pancreatic trypsin inhibitor. II. Crystallographic refinement at 1.9 A resolution. *J Mol Biol.* 89:73-101, 1974
27. Schmidt A E, Chand H S, Cascio D, Kisiel W, Bajaj S P. Crystal Structure of Kunitz Domain 1 (KD1) of Tissue Factor Pathway Inhibitor-2 in Complex with Trypsin: Implications for KD1 Specificity of Inhibition. *J Biol Chem.* 280:27832-27838, 2005
28. Wang, X., Lin, X., Loy, J. A., Tang, J., and Zhang, X. C. Crystal structure of the catalytic domain of human plasmin complexed with streptokinase *Science* 281, 1662-1665, 1998.
29. Bajaj, M. S., Birkctoft, J. J., Steer, S. A., and Bajaj, S. P. Structure and biology of tissue factor pathway inhibitor. *Thromb. Haemost.* 86, 959-972, 2001.
30. Beierlein W, Scheule A M, Dietrich W, Ziemer G. Forty years of clinical aprotinin use: a review of 124 hypersensitivity reactions. *Ann Thorac Surg.* 79:741-748, 2005.

What is claimed is:

1. A KD1 polypeptide comprising:
   (i) an amino acid sequence with at least 92% identity to SEQ ID NO:3 and in which arginine is present at position 17,
   (ii) an amino acid sequence with at least 92% identity to SEQ ID NO:3 and in which lysine, histidine or arginine is present at position 17, or
   (iii) an amino acid sequence with at least 92% identity to SEQ ID NO:3 and in which serine, threonine, asparagine, lysine, histidine or arginine is present at position 17,
   wherein the KD1 polypeptide inhibits plasmin activity and has decreased anti-coagulation activity as compared to a wild type KD1 polypeptide.

2. The KD1 polypeptide of claim 1, which is selected from (a) the KD1 polypeptide of claim 1 wherein the amino acid sequence has at least 93% identity to SEQ ID NO:3, (b) the KD1 polypeptide of claim 1 wherein the amino acid sequence has at least 94% identity to SEQ ID NO:3, (c) the KD1 polypeptide of claim 1 wherein the amino acid sequence has at least 95% identity to SEQ ID NO:3, (d) the KD1 polypeptide of claim 1 wherein the amino acid sequence has at least 96% identity to SEQ ID NO:3, and (e) the KD1 polypeptide of claim 1 wherein the amino acid sequence has at least 97% identity to SEQ ID NO:3.

3. The KD1 polypeptide of claim 1, wherein at least one of: (a) leucine is present at amino acid sequence position 18, (b) leucine is present at amino acid sequence position 19, (c) arginine is present at amino acid sequence position 31, and (d) leucine is present at amino acid sequence position 34.

4. The KD1 polypeptide of claim 1, which is selected from (a) the KD1 polypeptide of claim 1 wherein the amino acid sequence has at least 98% identity to SEQ ID NO:3, and (b) the KD1 polypeptide of claim 1 wherein the amino acid sequence has at least 99% identity to SEQ ID NO:3.

5. The KD1 polypeptide of claim 1, wherein the amino acid sequence is SEQ ID NO:3.

6. The KD1 polypeptide of claim 1, wherein the amino acid sequence comprises at least one substitution in the sequence set forth in SEQ ID NO:3 that is selected from the group consisting of: a tyrosine to glutamic acid substitution at position 46, a tyrosine to threonine substitution at position 11, an alanine to methionine substitution at position 16, an alanine to glycine substitution at position 16, an alanine to serine substitution at position 16, an aspartic acid to tyrosine substitution at position 10, and an aspartic acid to glutamic acid substitution at position 10.

7. The KD1 polypeptide of claim 6, wherein the amino acid sequence comprises a tyrosine to glutamic acid substitution at position 46.

8. The KD1 polypeptide of claim 6, wherein the amino acid sequence comprises a tyrosine to threonine substitution at position 11.

9. The KD1 polypeptide of claim 6, wherein the amino acid sequence comprises an alanine to methionine substitution at position 16.

10. The KD1 polypeptide of claim 6, wherein the amino acid sequence comprises an alanine to glycine substitution at position 16.

11. The KD1 polypeptide of claim 6, wherein the amino acid sequence comprises an alanine to serine substitution at position 16.

12. The KD1 polypeptide of claim 6, wherein the amino acid sequence comprises an aspartic acid to tyrosine substitution at position 10.

13. The KD1 polypeptide of claim 6, wherein the amino acid sequence comprises an aspartic acid to glutamic acid substitution at position 10.

14. The KD1 polypeptide of claim 1 which comprises the amino acid sequence set forth in one of SEQ ID NO:2, SEQ ID NO:3, and SEQ ID NO:4.

15. A KD1 polypeptide comprising an amino acid sequence with at least 93% identity to the KD1 amino acid sequence set forth as amino acids 10-67 of SEQ ID NO:1, wherein amino acid 26 of SEQ ID NO:1 is changed from leucine to arginine or lysine, and wherein the polypeptide inhibits plasmin activity and has decreased anti-coagulation activity as compared to a wild type KD1 polypeptide.

16. The KD1 polypeptide of claim 15, wherein the amino acid sequence has at least 94% identity to the KD1 amino acid sequence set as amino acids 10-67 of SEQ ID NO:1.

17. The KD1 polypeptide of claim 15, wherein the amino acid sequence has at least 95% identity to the KD1 amino acid sequence set forth as amino acids 10-67 of SEQ ID NO:1.

18. The KD1 polypeptide of claim 15, wherein the amino acid sequence has at least 96% identity to the KD1 amino acid sequence as amino acids 10-67 of SEQ ID NO:1.

19. The KD1 polypeptide of claim 15, wherein the amino acid sequence has at least 97% identity to the KD1 amino acid sequence set forth as amino acids 10-67 of SEQ ID NO:1.

20. The KD1 polypeptide of claim 15 which comprises the amino acid sequence set forth in SEQ ID NO:3.

21. The KD1 polypeptide of claim 15, wherein the amino acid sequence that has at least 93% identity to the KD1 amino acid sequence set forth as amino acids 10-67 of SEQ ID NO:1 comprises a substitution selected from the group consisting of a tyrosine to glutamic acid substitution at position 55 of SEQ ID NO:1, a tyrosine to threonine substitution at position 20 of SEQ ID NO:1, an alanine to methionine substitution at position 25 of SEQ ID NO:1, an alanine to glycine substitution at position 25 of SEQ ID NO:1, an alanine to serine substitution at position 25 of SEQ ID NO:1, an aspartic acid to tyrosine substitution at position 19 of SEQ ID NO:1, and an aspartic acid to glutamic acid substitution at position 19 of SEQ ID NO:1.

22. The KD1 polypeptide of claim 21, wherein the amino acid sequence that has at least 93% identity to the KD1 amino acid sequence set forth as amino acids 10-67 of SEQ ID NO:1 comprises a tyrosine to glutamic acid substitution at position 46 of SEQ ID NO:1.

23. The KD1 polypeptide of claim 22, wherein the amino acid sequence that has at least 93% identity to the KD1 amino acid sequence set forth as amino acids 10-67 of SEQ ID NO:1 comprises a tyrosine to threonine substitution at position 11 of SEQ ID NO:1.

24. The KD1 polypeptide of claim 23, wherein the amino acid sequence that has at least 93% identity to the KD1 amino acid sequence set forth as amino acids 10-67 of SEQ ID NO:1 comprises an alanine to methionine substitution at position 16 of SEQ ID NO:1.

25. The KD1 polypeptide of claim 24, wherein the amino acid sequence that has at least 93% identity to the KD1 amino acid sequence set forth as amino acids 10-67 of SEQ ID NO:1 comprises an alanine to glycine substitution at position 16 of SEQ ID NO:1.

26. The KD1 polypeptide of claim 25, wherein the amino acid sequence that has at least 93% identity to the KD1 amino acid sequence set forth as amino acids 10-67 of SEQ ID NO:1 comprises an alanine to serine substitution at position 16 of SEQ ID NO:1.

27. The KD1 polypeptide of claim 26, wherein the amino acid sequence that has at least 93% identity to the KD1 amino acid sequence set forth as amino acids 10-67 of SEQ ID NO:1 comprises an aspartic acid to tyrosine substitution at position 10 of SEQ ID NO:1.

28. The KD1 polypeptide of claim 27, wherein the amino acid sequence that has at least 93% identity to the KD1 amino acid sequence set forth as amino acids 10-67 of SEQ ID NO:1 comprises an aspartic acid to glutamic acid substitution at position 10 of SEQ ID NO:1.

29. The KD1 polypeptide of claim 15 which comprises the amino acid sequence set forth in one of SEQ ID NO:2, SEQ ID NO:3, and SEQ ID NO:4.

* * * * *